United States Patent
Tamtoro et al.

(10) Patent No.: US 11,207,460 B2
(45) Date of Patent: Dec. 28, 2021

(54) DRUG DELIVERY STORAGE DEVICE AND SYSTEM

(71) Applicant: AMGEN INC., Thousand Oaks, CA (US)

(72) Inventors: Ferry Tamtoro, San Ramon, CA (US); Huaying Yang, Vernon Hills, IL (US); Scott Robert Gibson, Granada Hills, CA (US); Donald Busby, Thousand Oaks, CA (US); Peter V. Shultz, Woodland Hills, CA (US); Basel Hasan Taha, Westlake Village, CA (US); Adam B. McCullough, Westlake Village, CA (US)

(73) Assignee: AMGEN INC., Thousand Oaks, CA (US)

(*) Notice: Subject to any disclaimer, the term of this patent is extended or adjusted under 35 U.S.C. 154(b) by 868 days.

(21) Appl. No.: 15/775,650

(22) PCT Filed: Dec. 14, 2016

(86) PCT No.: PCT/US2016/066490
§ 371 (c)(1),
(2) Date: May 11, 2018

(87) PCT Pub. No.: WO2017/106247
PCT Pub. Date: Jun. 22, 2017

(65) Prior Publication Data
US 2020/0289740 A1 Sep. 17, 2020

Related U.S. Application Data

(60) Provisional application No. 62/266,788, filed on Dec. 14, 2015.

(51) Int. Cl.
*G06F 17/00* (2019.01)
*A61M 5/00* (2006.01)
(Continued)

(52) U.S. Cl.
CPC ............ *A61M 5/002* (2013.01); *A61J 7/0418* (2015.05); *A61J 7/0436* (2015.05); *A61J 7/0481* (2013.01);
(Continued)

(58) Field of Classification Search
CPC ...... A61M 5/002; A61J 7/0418; A61J 7/0436; A61J 7/0481; A61J 2200/30; G16H 20/17; G16H 40/63
(Continued)

(56) References Cited

U.S. PATENT DOCUMENTS

| | | | |
|---|---|---|---|
| 9,161,885 B1 | 10/2015 | Zhou | |
| 2008/0099367 A1* | 5/2008 | Niemiec | ............ G08B 13/1427 206/528 |
| 2018/0333330 A1* | 11/2018 | Nagar | ........................ F25D 3/08 |

FOREIGN PATENT DOCUMENTS

| | | |
|---|---|---|
| WO | WO-2005046559 A2 | 5/2005 |
| WO | WO-2011133724 A2 | 10/2011 |

(Continued)

OTHER PUBLICATIONS

International Preliminary Report on Patentability and Written Opinion of the International Searching Authority for International Application No. PCT/US2016/066490, dated Jun. 19, 2018.
(Continued)

*Primary Examiner* — Tai T Nguyen
(74) *Attorney, Agent, or Firm* — Marshall, Gerstein & Borun LLP

(57) ABSTRACT

A drug delivery system includes a storage container defining one or more storage compartments and having at least one container sensor coupled thereto, a container condition change mechanism coupled to the storage container for imparting a change on one or more conditions of the one or more storage compartments, at least one drug delivery
(Continued)

device adapted to deliver a drug to a user and adapted to be at least partially disposed within one or more of the one or more storage compartments, at least one delivery device sensor, a delivery device condition change mechanism coupled to the drug delivery device, and a controller coupled to the storage container. The storage container may be adapted to hold a number of drug delivery devices within a number of sealable storage compartments. The container sensor is adapted to sense a condition of the storage container, and the delivery device sensor is adapted to sense a condition of the at least one drug delivery device. The controller is adapted to instruct the container condition change mechanism and/or the delivery device change mechanism to impart a change on at least one condition of the storage container and/or the drug delivery device.

20 Claims, 10 Drawing Sheets

(51) Int. Cl.
*A61J 7/04* (2006.01)
*G16H 20/17* (2018.01)
*G16H 40/63* (2018.01)

(52) U.S. Cl.
CPC ............ *G16H 20/17* (2018.01); *G16H 40/63* (2018.01); *A61J 2200/30* (2013.01); *A61J 2200/42* (2013.01); *A61J 2200/44* (2013.01); *A61J 2200/70* (2013.01); *A61J 2200/72* (2013.01); *A61J 2205/60* (2013.01); *A61M 2205/0216* (2013.01); *A61M 2205/14* (2013.01); *A61M 2205/18* (2013.01); *A61M 2205/3306* (2013.01); *A61M 2205/3327* (2013.01); *A61M 2205/3331* (2013.01); *A61M 2205/3368* (2013.01); *A61M 2205/3584* (2013.01); *A61M 2205/3606* (2013.01); *A61M 2205/3673* (2013.01); *A61M 2205/50* (2013.01); *A61M 2205/502* (2013.01); *A61M 2205/52* (2013.01); *A61M 2205/6054* (2013.01)

(58) Field of Classification Search
USPC ........................................................ 700/240
See application file for complete search history.

(56) References Cited

FOREIGN PATENT DOCUMENTS

| | | |
|---|---|---|
| WO | WO-2014152704 A1 | 9/2014 |
| WO | WO-2014197774 A2 | 12/2014 |
| WO | WO-2015061389 A1 | 4/2015 |
| WO | WO-2015187793 A1 | 12/2015 |

OTHER PUBLICATIONS

Written Opinion of the International Searching Authority and International Search Report for International Application No. PCT/US2016/066490, dated Apr. 11, 2017.

\* cited by examiner

DRUG DELIVERY STORAGE DEVICE AND SYSTEM

CROSS-REFERENCE TO RELATED APPLICATIONS

This is the U.S. national phase of International Patent Application No. PCT/US2016/066490, filed Dec. 14, 2016, which claims the priority benefit of U.S. Provisional Patent Application No. 62/266,788, filed Dec. 14, 2015, the entire contents of each of which are incorporated herein by reference.

BACKGROUND

The present disclosure is directed to systems and methods for utilizing smart storage devices with drug delivery devices.

Drugs may be administered through the use of drug delivery devices, such as autoinjectors or on-body injectors or infusers. These devices may replace older delivery systems using a combination of a syringe and a vial of the drug or medicament, or a pre-filled syringe. Autoinjectors and on-body injectors may be used to automate the injection and delivery or administration process, thereby simplifying the process for certain patient groups or sub-groups for which use of the syringe/vial combination or pre-filled syringe systems would be disadvantageous, whether because of physiological or psychological impediments.

Even with the use of drug delivery devices, such as autoinjectors, patients may experience challenges during the initial use of the drug delivery device after they have been prescribed a drug that is delivered or administered through the use of one of these devices. For example, the user may be uncertain as to whether the medication inside the drug delivery device is the medication prescribed for them. Additionally, the user may be uncertain whether the medication has expired. Further, the user may be uncertain whether the injection should be delayed after a drug delivery device has been removed from cold storage, such as in a refrigerator, and if the injection should be delayed, how long it should be delayed. The user may also be uncertain if the actions and their sequence correctly operate the drug delivery device. Even if the correct actions are performed in the correct sequence, the user may be uncertain the drug has been completely delivered, such that the injection is complete.

Patients may be hesitant to administer these drugs due to warming techniques which may result in risking administering a cold injection or require extended delivery times if the patient fails to wait an appropriate length of time after removing the device from refrigeration. These contributing factors which may extend the time of the perceived injection experience or add discomfort to the user may risk reducing adherence to therapy.

Patients desire both a comfortable and predictable injection experience. Administering injections using devices at substantially similar temperatures often yields substantially similar experiences. Differences of medicant temperatures at the time of administration of approximately 5° C. or more are likely to cause discernible differences to the patient, particularly in medicants having highly temperature-dependent viscosities, which may lead to hesitation and uncertainty in administering subsequent doses. This in turn may lead to reduced adherence levels.

Other patients may experience additional challenges in being adherent or compliant with the treatment regimen. For example, some patients may not perform the injections according to the treatment regimen or may have entirely forgotten to perform the injection in adherence with the prescribed schedule. Other patients may perform the injections, but may subsequently be unable to recall whether they performed the injections due to distractions occurring before they are able to record the completed injection. Some patients may elect not to perform the injections due to misunderstandings or miscommunications of when or how the medication will affect the patient's disease or symptoms, especially where the effects are not felt by the patient until a considerable amount of the treatment regimen has been performed. Some patients may require support and/or encouragement from others (healthcare provider, caregiver, family member, etc.), which support and/or encouragement may not be provided because the people that would provide that support and/or encouragement are not aware of whether the patient has performed the treatment or if the treatment regimen has been followed correctly.

In addition, the condition and use of drug delivery devices is of importance to other parties, such as drug device manufacturers, pharmacies, health care providers and insurers. For instance, information regarding the condition of the drug delivery device along the supply chain may be relevant to whether the drug delivery device will be in good working order when it arrives for use with the patient. Information regarding the location of the drug delivery device along the supply chain may be relevant to the manufacturer and the pharmacy to ensure that adequate supplies are available for the pharmacy to delivery to the user. The compliance information mentioned above may be important to the healthcare providers and insurers, as well as to the patient, because compliance with a therapy regimen may have a direct impact on the success of the therapy.

As set forth in more detail below, the present disclosure describes a drug delivery system and approaches embodying advantageous alternatives to existing drug delivery device packaging that may address one or more of the above challenges or needs.

SUMMARY

Opportunities may exist for "smart" packaging and storage to add value to combination products. Changes to packaging or containers may be made quicker to packaging than to drug delivery devices, and the environmental impact may be reduced while accomplishing a similar outcome due to the packaging being less damaging to the environment and even reusable or recyclable.

In many of these examples, smart packaging for drug delivery devices may identify a number of units or delivery devices remaining of a multi-pack, communicate to a user (for example, via a mobile computing device) that it is time to take a dosage of the drug, predict the temperature of the drug and alert the user of when the drug has reached an acceptable use temperature, track the total temperature excursion time, facilitate rapid warming or cooling of the drug delivery device, and communicate with controllers, processors, and/or remote computing devices to assist in patient journaling.

According to some embodiments, a drug delivery system includes a storage container defining at least one storage compartment, at least one container sensor coupled to the storage container for sensing a condition of the at least one storage compartment, a container condition change mechanism coupled to the storage container for imparting a change on one or more conditions of the one or more storage compartments, at least one drug delivery device adapted to deliver a drug to a user, at least one drug delivery device sensor coupled to the drug delivery device, a delivery device condition change mechanism coupled to the at least one drug delivery device for imparting a change on one or more conditions of the at least one drug delivery device, and a controller coupled to the storage container. The controller is in communication with the at least one container sensor and the at least one delivery device sensor when the at least one drug delivery device is disposed in one or more of the storage compartments. The controller may include a memory, a processor, and computer-executable instructions stored on the memory and executable by the processor to instruct at least one of the container condition change mechanism to impart a change on the one or more conditions of the one or more storage compartments of the storage container and the delivery device condition change mechanism to impart a change on the one or more conditions of the at least one drug delivery device.

In some examples, the controller may cause the storage container to change temperature, alert a user of the sensed condition, log the sensed condition and/or transmit the sensed condition to a remote computing device. The controller may also present information to a user and/or determine an appropriate time to use the drug delivery device. Other examples are possible.

The at least one container sensor may be any number of sensors such as proximity sensors coupled to the storage container for sensing at least one of a presence of the at least one drug delivery device and whether the storage container is in an open configuration, pressure sensor conductive switches disposed within the storage container for sensing whether the drug delivery device is disposed within the storage container, temperature sensors coupled to the storage container for sensing at least one of an external temperature and an internal temperature of the storage container, superelastic materials adapted to engage a circuit when the housing is within a temperature threshold, and/or humidity sensors for sensing a humidity within any number of compartments of the storage container, and the like. Other examples are possible. The drug delivery device sensor or sensor may similarly include any of these sensors.

The container condition change mechanism may include (a) a heating mechanism which raises the temperature of the one or more storage compartments, a cooling mechanism which lowers the temperature of the one or more storage compartments, a locking mechanism which selectively restricts and permits access to the one or more storage compartments, and/or a communication and/or audiovisual device adapted to present information relating to the drug delivery system. Other examples are possible. Similarly, the delivery device condition change mechanism may include any of these mechanisms.

In some approaches, each of the one or more storage compartments includes a sealing mechanism to selectively thermally and/or hermetically seal the storage compartment. In some examples, the sealing mechanism may simply be a lid adapted to cover at least a portion of a surface of the storage container. Other examples are possible.

The drug delivery system may include any number of drug delivery devices, each having a delivery device sensor coupled thereto. The storage container may include a number of sealable storage compartments which may be thermally sealed relative to each other and a number of container sensors associated with each of the sealable storage compartments.

The storage container may further include a number of accessories, such as, for example, a display adapted to display information related to the drug delivery system. The display may display an indication that the drug delivery device is ready for use, an indication of when the drug delivery device will be ready for use, and/or an indication of a quantity of drug delivery devices remaining for use. Other examples of information that may be displayed are possible. The storage container may also include one or more charging devices that may provide recharging power to the at least one drug delivery device.

In some examples, the storage compartments may be one or more drawers adapted to be selectively opened. These drawers may each be adapted to hold at least one drug delivery device.

In many of these approaches, a first communication module coupled to the storage container and a computing device located separate from the storage container and the at least drug delivery device is provided. The computing device may also have a memory, a processor, computer-executable instructions stored on the memory, and a second communication module adapted to communicate with the first communication module. In these approaches, The controller may instruct the first communication module to transmit a signal to the second communication module of the computing device, and the computing device may be adapted to determine and transmit a corresponding signal via the second communication module to the first communication module to instruct the container condition change mechanism and/or the delivery device condition change mechanism to impart a change.

In other examples, a drug delivery system is provided including a storage container defining one or more storage compartments, at least one container sensor coupled to the storage container for sensing a condition of the storage container, and a container condition change mechanism coupled to the storage container for imparting a change on one or more conditions of the one or more storage compartments. The drug delivery system may further include at least one drug delivery device adapted to deliver a drug to a user and adapted to be at least partially disposed within one or more of the one or more storage compartments, at least one delivery device sensor coupled to the at least one drug delivery device for sensing a condition of the drug delivery device, and a delivery device condition change mechanism coupled to the at least one drug delivery device for imparting a change on one or more conditions of the at least one drug delivery device. Further still, the system may include a first communication module coupled to the storage container, a computing device located separate or remotely from the storage container and the at least one drug delivery device, and a computing device having a second communication module which is adapted to communicate with the first communication module. The computing device may include a memory, a processor, and computer-executable instructions stored on the memory. A controller is also provided which is coupled to the first communication module and is adapted to receive a signal from the storage container sensor and/or the delivery device sensor and may cause the first communication module to transmit a signal to the computing device. The second communication module may be adapted to determine and transmit a corresponding signal to the first communication module to instruct the container condition change mechanism to impart a change on the one or more conditions of the one or more storage compartments of the storage container and/or the delivery device condition change mechanism to impart a change on the one or more conditions of the at least one drug delivery device.

In many approaches, the computing device may be a mobile phone, a tablet, a personal computer, and/or a cloud-based server. Other examples are possible.

In some of these examples, the storage container may restrict the first communication module from transmitting the signal to the computing device when the storage container is in a closed configuration. The first communication module may transmit the signal using a wireless communication protocol. The signal transmitted to the computing device may include information relating to a temperature excursion experienced within the storage container, a frequency of use of the delivery device, and/or a quantity of unused delivery devices. Other examples are possible.

In some of these approaches, the controller may be adapted to identify a particular drug delivery device amongst a plurality of drug delivery devices as having an earliest expiration date. The controller may then cause this delivery device to be selectively warmed so as to use expiring drugs sooner. In many of these approaches, the drug delivery devices may be thermally isolated from each other to allow for selectively warming the devices. In some examples, the storage container may be vacuum sealed and pumped to create a thermally isolated area therein.

In some embodiments, the drug delivery device may be reusable. In these embodiments, the storage container may further include a charging device which provides recharging power to the drug delivery device. Additionally, the drug delivery system may include a power source that provides power to the system. An alternative source of power (e.g., a battery backup system) may also be incorporated to provide power to the system should the primary source of power incur a failure.

In yet other examples, an approach for managing a plurality of drug delivery devices stored in a plurality of compartments in a storage container is described and includes obtaining data from each of the plurality of drug delivery devices using a controller coupled to the storage container, based on the obtained data, determining a particular one of the plurality of drug delivery devices to effect an action upon, and selectively instructing at least one of a container condition change mechanism coupled to the container to impart a change on one or more conditions of the plurality of compartments and a drug delivery device condition change mechanism coupled to at least one delivery device to impart a change on one or more conditions of the drug delivery device.

In some of these approaches, selectively instructing the container change mechanism to impart a change my include displaying, via a display, information relating to the sensed condition, adjusting the temperature of at least one of the plurality of compartments in the storage container, restricting and/or granting access to the storage container by locking a lid, and/or providing, via an alert device, a user with information relating to at least one drug delivery device. Further, selectively instructing the container change mechanism to impart a change my include selectively granting access to a particular drug delivery device stored in a particular compartment, logging the sensed condition, transmitting the sensed condition to a remote computing device, and/or determining an appropriate time to use the drug delivery device. Other examples are possible.

In some of these approaches, selectively instructing the delivery device change mechanism to impart a change my include selectively adjusting a temperature of at least one drug delivery device, selectively enabling at least one of the drug delivery devices, selectively enabling at least one of the drug delivery devices in response to user identify information input received from a user, selectively disabling at least one of the drug delivery devices, selectively disabling at least one of the drug delivery devices at least until verifying identity information received via a user input, and/or communicating an enabled/disabled status of at least one of the drug delivery devices to the alert device. Other examples are possible.

The container sensor or sensors may be adapted to detect any one of a presence of the drug delivery device in the at least one sealable storage compartment, whether the storage container is presently in an open or closed configuration, whether the at least one drug delivery device is disposed within the storage container, an ambient temperature surrounding the storage container, and/or an internal temperature within the storage container. The container sensor may also be adapted to determine whether the storage container is in a sealed or unsealed configuration, and/or a temperature differential within the storage container and an outside environment. Other examples are possible. In some embodiments, a plurality of container sensors may be utilized.

The at least one delivery device sensor may obtain data relating to a quantity of drug contained within the delivery device and/or a temperature of the drug delivery device. Other examples are possible. Further, any number of delivery device sensors may be used.

In many examples, the data obtained and selective instructions are communicated via wired and/or wireless communication protocols. The displayed information may relate to an indication that the drug delivery device has reached a threshold temperature and is ready for use, an indication of when the drug delivery device will be ready for use, and/or an indication of a quantity of drug delivery devices remaining for use.

In many of these approaches, a controller may be provided which is adapted to read identification information for each of the plurality of drug delivery devices, compare the identification information of each of the drug delivery devices, and identify a drug delivery device amongst the plurality of drug delivery devices as having an earliest expiration date. Determining the particular one of the plurality of drug delivery devices includes determining the drug delivery device having the earliest soonest or expiration date. The effected action may include selectively adjusting a temperature of any number of compartments in the storage container and selectively providing access to any number of compartments in the storage container. Other examples are possible.

The controller may cause the storage container to change temperatures by any combination of passive heating, active convection heating, and/or active reverse cooling. The storage container may also have any number of cooling systems to keep the drug delivery devices at a lowered resting temperature. Other examples are possible.

In many approaches, upon opening the storage container, a monitoring circuit may be activated which may cause at least one of the container sensor and the device sensor to be activated.

In still further examples, a container for selective storage of a plurality of drug delivery devices, each of which having at least one device sensor and at least one communication module for transmitting information collected by the device sensor is provided. The container includes a container sensor being adapted to sense a condition of the container and being at least partially disposed within the container, and a controller coupled to the container sensor and the at least one device sensor. The controller may be adapted to receive a sensed condition of the container sensor and/or the device sensor and, upon the sensed condition reaching a threshold value, transmit a control command to provide an alert indicating the sensed condition has been met.

The sensed condition may include conditional state information and/or operational state information. The alert device may comprise a display which displays the control command transmitted thereto.

In some alternatives, the container may further include a temperature adjustment device. The controller may be adapted to transmit a control command to the temperature adjustment device to adjust the temperature of at least one of the drug delivery devices selectively stored in the container.

In further embodiments, a drug delivery device storage system includes a storage container defining one or more compartments, at least one container sensor coupled to the storage container being adapted to sense a condition of the container, and a controller coupled to the storage container. The controller is in communication with the at least one container sensor and may include a memory, a processor, and a communication module. The controller is adapted to receive the sensed condition of the container and transmit a signal containing a representation of the sensed condition. In some approaches, a drug delivery device may be provided which is adapted to be placed in the storage container after the drug delivery device is used.

The container sensor may include an accelerometer which is adapted to sense a movement of the storage container. The communication module may be adapted to transmit the sensed data to a remote computing device, which may be at least one of a personal computing device, a remotely located server, a mobile communication device, and/or a tablet computer. In some forms, the storage system may include a coupling device which may communicatively couple the container sensor to the remote computing device.

BRIEF DESCRIPTION OF THE DRAWINGS

The above needs are at least partially met through provision of the smart packaging for combination product described in the following detailed description, particularly when studied in conjunction with the drawings, wherein.

Figure 1:
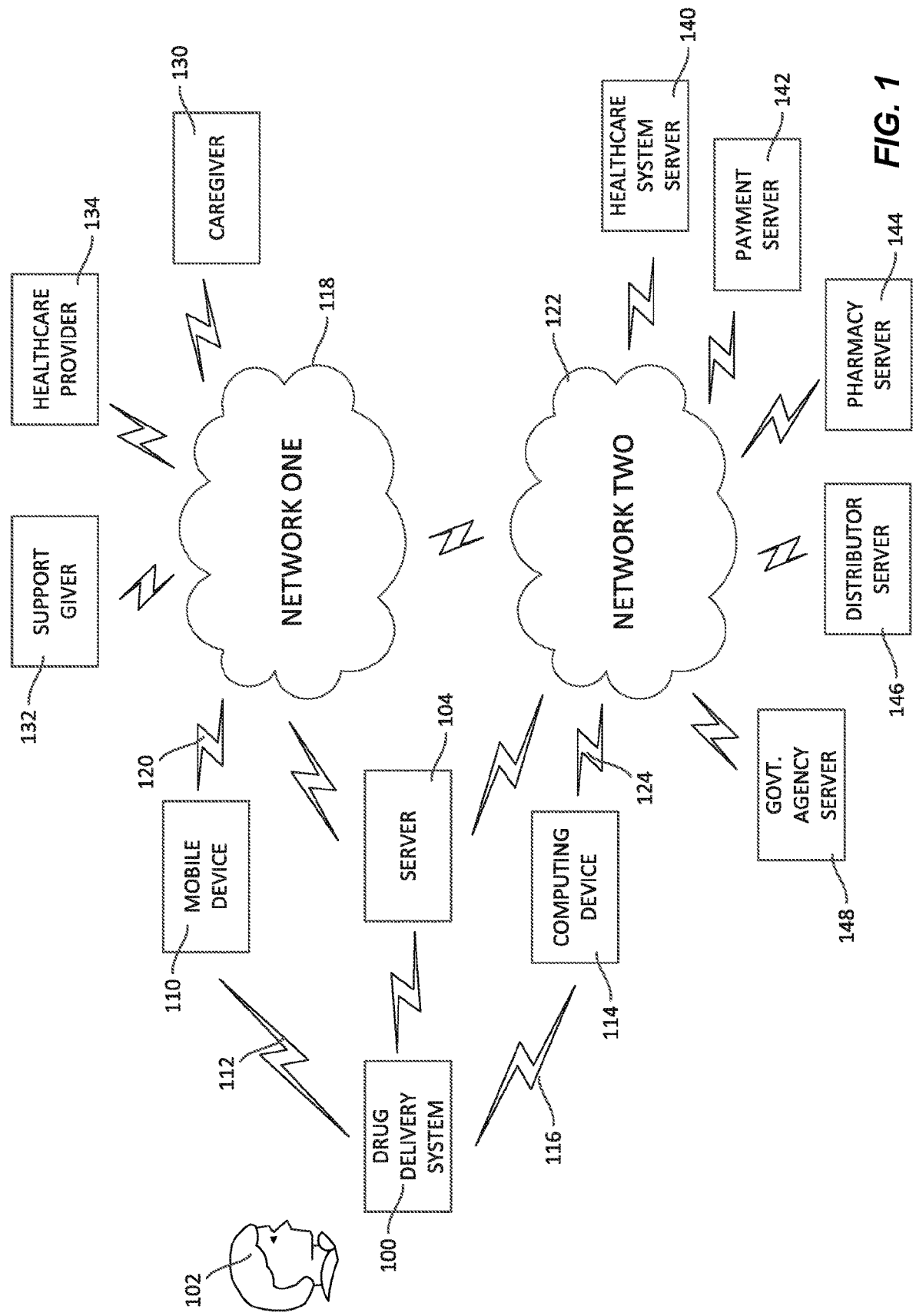
FIG. 1 comprises a schematic diagram of a drug delivery system according an embodiment of the disclosure in communication with one or more computing devices and one or more networks in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

This disclosure is directed to a plurality of systems including a drug delivery device and its corresponding container, as well as a number of approaches for using the systems. In particular, the systems and approaches involve the use of packaging which stores, senses and/or monitors, and affect any number of actions on the drug delivery devices to better enhance a user's experience when administering the drugs via the drug delivery devices. The sensors may rely on mechanical, electrical, or chemical sensing mechanisms, and the controller or controllers themselves may similarly be mechanical, electrical, and/or electromechanical. As a non-limiting example, the container or packaging which houses the drug delivery device may determine any number of conditional and/or operational states of the drug delivery device. The approaches described herein may use this state determination to control the operation of the drug delivery device and/or selective aspects of the container, and further may communicate the state determination to other devices such as third-party servers responsible for collecting, processing, and/or further disseminating the information received. The approaches described may further communicate this determined information to local computing devices, such as, for example, cellular telephones, computers, tablets, and the like.

In some examples, traditional disposable packaging may be used in conjunction with a storage container. Both the disposable packaging and the storage container may be integrated with any number of passive and/or active communication modules and sensors (e.g., temperature and/or proximity sensors) associated with a time differential based on the opening of a storage container. These approaches may generate a timestamp or other indicator upon opening the package, and may detect or predict acceptable injection temperature timing. A computing device may record the removal of the injection device, and the data may be used to better determine use profiles. As a result, a user may obtain a better understanding of appropriate timing, and may receive automatic incentives to use and reorder the drug when necessary.

In other approaches, a container or case may be utilized in conjunction with reusable delivery devices and packaging. These devices may communicate via wired and/or wireless communication protocols. In these approaches, the container may provide charging power to the delivery device and may further protect the delivery device when not in use between doses. The container may be adapted to identify a particular medicant cartridge placed inside the container, and obtain appropriate information (e.g., usage and/or identifying information). The container and/or device may communicate audiovisual messages including usage instructions.

Additionally, the container may expedite warming of the medication in a controlled manner and alert the patient when the dose is ready for administration. The user may also be reminded when a subsequent medication should be administered.

In still further embodiments, an administration accessory may be provided which removes the burden or storing medication amongst food items and may provide for discreet storage and dosage facilitation. As before, the accessory may communicate via wired or wireless communication protocols. The devices may include components suitable for heating and/or cooling the delivery devices, and also provide thermal isolation of individual doses to enable individual temperature adjustments. A user may schedule appropriate warming cycles and administration of dosages remotely to enable comfortable drug delivery during a shortened period.

In one exemplary embodiment, a drug delivery system according to the disclosure may include a drug delivery device having a reservoir (which may also be referred to as a primary container, e.g. a syringe, vial or cartridge). The reservoir may contain a drug, which may also be referred to as a medication or a medicament. The drug may be one of, but is not limited to, various biologicals such as peptides, peptibodies, or antibodies. The drug may be in a fluid or liquid form, although the disclosure is not limited to a particular state (e.g., no differentiation is intended between a solution, a gel, or a lyophilized product for example). The drug delivery device may also include a delivery cannula having a first end connected to or connectable in fluid communication with the reservoir and a second end to be inserted within a patient. As used herein, the term "delivery cannula" or "cannula" is hereby defined to mean a tube that can be inserted into the body for the delivery of fluid. A cannula may include a rigid or semi-rigid needle or blunt cannula, or may be in a flexible form, by example and not by way of limitation. The cannula may be integrated with the other elements of the drug delivery device, or the cannula may be separate from the other elements of the drug delivery until immediately prior to use. According to certain embodiments, the drug delivery device may further include an inserter to introduce the second end into the patient, although this is not required according to each embodiment of the disclosure. The inserter may or may not be withdrawn back into the device, thereby leaving the cannula in a patient.

Considering the foregoing description of the drug delivery device, the device may be characterized as an autoinjector or an on-body injector or infuser (the reference to injector intended to include also a reference to an infuser, to the extent that a difference is suggested). Autoinjectors may be single-use devices which administer a single dose during a single application of the device to the user's skin, although autoinjectors are not limited to only single-use devices—they may be multi-use devices as well. On-body injectors may be multi-use devices, administering multiple doses during one or more applications of the device to the user's skin, although on-body devices may also be used as single-use devices. Either autoinjectors or on-body injectors may have assemblies or sub-assemblies that are reusable, in that the assemblies may be used and re-used by refilling the reservoir, by removing an empty reservoir and replacing it with a filled reservoir, or by replacing the cannula, for example.

As previously noted, the approaches described herein may determine at least one state relative to the drug delivery device. For example, approaches may determine if the drug delivery device is in one or more operational states (i.e., a state relating to the operation of the drug delivery device to deliver the drug to the patient). A non-exhaustive list of the general operational states may include (i) packaged/ready for distribution; (ii) packaged/distributed; (iii) unpackaged/ready for administration; (iv) sterile barrier removed; (v) device applied; (vi) cannula injected (or inserted); (vii) drug delivery initiated; (viii) drug delivery completed; and (ix) device removed. The system or method may determine specific operational states within each of the general operational states; for example, the system or method may determine if plunger has been moved from a first end of a bore (defining a drug reservoir) to a second end of the bore to determine if the drug delivery device is in the "drug delivery complete" state.

Further the approaches described herein may determine if the drug delivery device is in one or more condition states (i.e., a state relating to the condition of the drug delivery device, not necessarily related to the operation of the drug delivery device to deliver the drug to the patient). A non-exhaustive list of condition states may include (i) age (e.g., taken with respect to a manufacturing date or an expiration date); (ii) sterility/contamination; (iii) temperature (or temperature history); and (iv) orientation. The determination of a condition state may be considered as part of the determination of an operational state; for example, the determination of the temperature state may be considered as part of the determination of the "ready for administration" state. Alternatively, the operational and condition states may be separately determined.

These states may be determined through the use of one or more sensors. These sensors may either be disposed within or coupled to the container and/or may be disposed within or coupled to the delivery device. The sensors may be particular to a condition state to be determined: for example, a thermocouple disposed adjacent to the reservoir may be used to determine the temperature state of the drug delivery device. The sensors may be particular to an operational state to be determined: for example, a switch may be coupled to a needle guard to determine when a needle cap has been removed to determine the "sterile barrier removed" operational state, the switch being open when the needle cap is disposed over the second end of the cannula and the switch being closed when the needle guard is not disposed over the second end of the cannula. Sensors may be used to determine both a condition state and an operational state: for example, the thermocouple may be used to determine the temperature condition state of the device (or more particularly, the drug), and/or the thermocouple may be used to determine the "ready for administration" operational state.

In many examples the determined states may be used to control the operation of the container and/or drug delivery device. For example, the system may include a controller that is coupled to the sensor and/or sensors and may be coupled to one or more of the assemblies or subassemblies of the drug delivery device described above, or to one or more additional assemblies or subassemblies of the drug delivery device. The controller may be adapted structurally or programmed (if electrical or electro-mechanical) to activate or to inhibit these assemblies or subassemblies in accordance with the determined states. For example, the drug delivery device may include a lockout that limits or completely inhibits the operation of the injector, and the controller may activate the lockout in a reversible fashion if the temperature state of the drug delivery device (and in particular, the drug in the reservoir) is below a threshold state. The system may also selectively adjust the temperature of a particular area or compartment of the container in which a particular delivery device is disposed.

In many embodiments, the determined state(s) may be communicated to other devices and/or systems, which may be performed in conjunction with use of the determined state(s) to control the operation of the drug delivery device. For example, the determined state(s) may be communicated via a networked device using a communication link or protocol. In this sense, a networked device is intended to include any device that communicates with at least one other device over a communication link, and might include communication with a device such as mobile device (e.g., cell phone or mobile computing device) using a Bluetooth connection or a computing device using a Wi-Fi connection, for example. The networked device may communicate the determined states to other computing devices remote from the drug delivery system over the network that includes the networked device such as a server. According to certain embodiments of the present disclosure, the system communicates directly with the network (i.e., without an intermediate networked device—the system itself is a networked device) or directly with a remote computing device such as a server (using, for example, a 2G, 3G, and/or 4G antenna). The state information communicated over network may then be used, for example, to determine if a patient is in compliance, or if a class of drug delivery devices is exhibiting a systemic malfunction. Other uses for the state information are possible.

Referring now to the drawings, and in particular to FIG. 1, a drug delivery system 100 is provided according to an embodiment of the disclosure. The drug delivery system 100 may be associated with a patient 102, who may use the drug delivery system 100 to inject a drug as part of a therapeutic regime. The drug delivery system 100 may communicate with a computing device (e.g. server) 104 via one or more intermediate computing devices and/or one or more networks. In turn, the server 104 may communicate with the drug delivery system 100, the patient 102, and one or more computing devices (with their associated parties) via one or more intermediate computing devices and/or one or more networks. As is also illustrated in FIG. 1, the server 104 may communicate directly with the drug delivery system 100, using a 3G antenna for example.

The drug delivery system 100 is illustrated as communicating with a mobile computing device 110 (e.g., a smartphone) via a first communication link 112, and with a computing device (e.g., a personal computer or dedicated hub) 114 via a second communication link 116. Both links 112, 116 may operate according to a near field communication protocol, such as Bluetooth, for example. The mobile computing device 110 may communicate with a cellular network 118 via a communication link 120, while the other computing device 114 may communicate with a hard-wired network (e.g., local area network or wide area network) 122 via a communication link 124. These networks 118, 122 may also communicate with the server 104.

The networks 118, 122 may facilitate communication between the server 104 and one or more parties associated with the patient 102, such as his or her caregiver 130, support giver 132, and healthcare provider 132, via their mobile computing devices (e.g., smartphones). The server 104 may also be in communication with one or more computing devices (e.g., servers) associated with one or more additional parties associated with the patient 102. For example, a healthcare system server 140, a payment server 142, a pharmacy server 144, a distributor server 146, and a governmental agency server 148 are illustrated in communication with the server 104 via the network 122. It will also be recognized that the networks 118, 122 may be in communication with each other.

Figure 2:
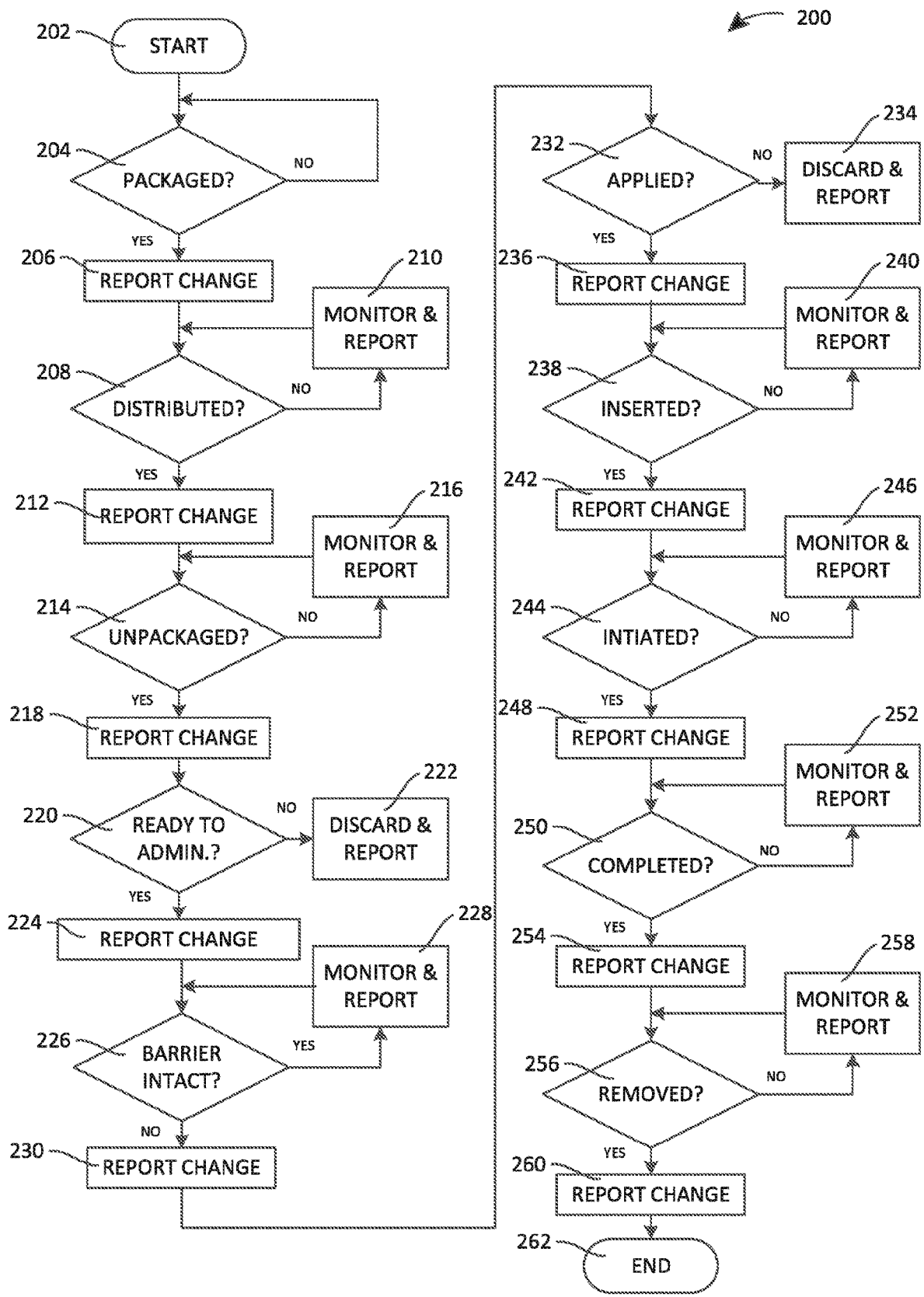
FIG. 2 comprises a block diagram of a method of operating a drug delivery system in accordance with various embodiments of the invention.

Referring to FIG. 2, possible methods of operating one or more computing devices in communication with a drug delivery system are now discussed in the context of a method 200. It will be recognized that the method 200 may be carried out by a single computing device, such as the server 104 illustrated in FIG. 1. Alternatively, the actions discussed with respect to FIG. 2 may be carried out by multiple computing devices, such as the mobile device 110 or computing device 114 in conjunction with the server 104.

The method 200 begins at block 202 with a determination as to whether a report has been received from the drug delivery system. If no report has been received, the method 200 waits at block 202. Once it is determined that a report has been received at block 202, the method 200 proceeds to block 204.

At block 204, the report received from the drug delivery system is used to update one or more records. In this regard, the one or more computing devices adapted or programmed to carry out the method 200 may perform the actions of retrieving the one or more records from storage in one or more memory storage devices, writing the information received from the drug delivery device into the one or more records, and then storing the one or more records in the one or more memory storage devices. The one or more memory storage devices may be part of the one or more computing devices, may be separate from the one or more computing devices, or may include one or more of the memory storage devices that are part of the one or more computing devices and one or more memory storage devices that are separate from the one or more computing devices (i.e., the record is stored at the computing device and in backup storage separate and possibly remote from the computing device).

As mentioned above, the report may be used to update one or more records. For example, there may be one record for the individual patient that is stored in a patient record database. The patient record may be used, for example, to track the compliance of the individual patient (e.g., patient 102) with his or her regime(s). There may also be a record for the drug delivery system used by the individual patient that is stored in a drug delivery system database. The drug delivery system record may be used to store information regarding the drug delivery system throughout the life of the drug delivery system. The drug delivery system record may be accessed by the drug delivery system manufacturer or the drug provider for quality control purposes (e.g., to monitor individual instances of the drug delivery system for faults or failures attributable for to the drug delivery system, or to track the environmental condition histories of one or more drug delivery systems for patterns that may assist in determining improvements in the design, packaging, shipment or handling of the drug delivery systems). There may also be record for drug used in the drug delivery system that is stored in a drug database. This record may be used in a similar fashion to the drug delivery system record for quality control purposes.

In addition to the updating the records at block 204, the computing device adapted or programmed to carry out the method 200 may be adapted or programmed to carry out one or more actions based on the information in the report received from the drug delivery system. For example, the computing device may be adapted or programmed to carry out an action at block 206. This action may require not only the information received in the report and/or stored previously in the record updated at block 204, but may require additional information such as from other patient records, drug system delivery records and/or drug records. If this is the case, the determination may be made at block 208 that these other records need to be accessed, and the information retrieved at block 210 (e.g., by retrieving these other records from the patient, drug delivery system and drug databases and reading the information from these records once retrieved). The action may then be carried out at block 222.

As one example, the one or more computing devices adapted or programmed to carry out the method 200 may be adapted or programmed to use the information received in the report to prepare a compliance history for the patient, which compliance history tracks uses of instances of the drug delivery system by the individual patient relative to his or her treatment regime to determine how successful the patient has been in following the treatment regime and which compliance history may be stored in the patient record. In addition, the one or more computing devices may determine if a pharmacy should be contacted to order delivery of additional drug delivery devices for the individual patient, and may generate a communication to be sent to the pharmacy to order the delivery of additional drug delivery systems. Further, the one or more computing devices may determine if a reminder should be sent to the patient, via the mobile device 110 for example, to improve or support compliance with the individual patient's treatment regime, in which case the one or more computing devices may generate a communication to be sent to the patient or user of the device. Further, the one or more computing devices may determine that the operation of the drug delivery device should be modified because of a conditional state received from the drug delivery device, for example. For example, the one or more computing devices may determine that the drug delivery system should be locked to prevent its use because of the temperature history of the drug in the drug delivery system, for example. In this case, the one or more computing devices may generate a communication, in the form of a signal for example, to be sent to the drug delivery system to lock the drug delivery device that is part of the drug delivery system. Other possible actions are discussed in detail below, although this discussion is for illustrative purposes only and is not intended to be limiting.

Depending on the action taken at block 212, or even if it is determined at block 206 that no action need be taken, the method 200 may proceed to blocks 214, 216, 218 where determinations are made if the computing device should make contact with other parties (block 214), interact with the patient (or user, if not the same as the patient) (block 216) or control the drug delivery device that is part of the drug delivery system (block 218). For example, as discussed above, the action taken at block 212 may involve the generation of communications or signals to be sent to third parties, such as the pharmacy, to the patient, or to the drug delivery device. In such a case, the one or more computing devices may carry out the actions of block 220, 222, 224 as dictated by the determinations made at blocks 214, 216, 218. Alternatively, the one or more computing devices may carry out the actions of blocks 220, 222, 224 even if it is determined that no action need be taken at block 206. For example, the one or more computing devices may forward certain information to third parties 220 based solely on the receipt of the information in a report from the drug delivery device, such that there is no need to separately determine that an action need be taken in regard to the information received (i.e., the communication is automatically sent based on the fact that the information has been received, with the one or more computing devices acting as a repeater station for such information). The receipt of information from the drug delivery device may also prompt communications to be sent to the patient/user or control signals to be sent to the drug delivery system without a separate determination that such action need be taken, the communication or control signal being sent simply because certain information and/or reports were received from the drug delivery system.

Having made the determinations at blocks 214, 216, 218 and carried out the actions of blocks 220, 222, 224, the method 200 may return to block 202 to await the next report. It will be recognized that the one or more computing devices may perform the actions of the method 200 in parallel for each of the reports received from different instances of the drug delivery system, or may perform this steps in sequence for each report. If performed in parallel, the one or more computing devices may determine if action is to be taken in regard to one report, while the one or more computing devices may be interacting with another patient in regard to the information contained in the report received from that patient. Furthermore, the one or more computing devices carrying out the method 200 need not be adapted or programmed to carry out each of the actions described above according to every embodiment of the one or more computing devices. For example, one of the one or more computing devices may be adapted or programmed to update records for each patient and to determine if an interaction with that patient is required, while another of the one or more computing devices may be adapted or programmed to update records for each drug delivery device and to determine is a control signal should be sent to the drug delivery device, while another one of the one or more computing devices does not update any record, but is adapted or programmed to access, for example, a patient record and determine if the pharmacy needs to be contacted to order additional instances of the drug delivery system for the patient associated with the patient record accessed and to generate the communication if the order of additional instances of the system is required.

It will be appreciated that the method 200, above, touches only a fraction of the possible state and identity information that may be used to control and/or monitor the drug delivery device and that may be communicated between the drug delivery system and the one or more computing devices, as well as how that information is used by the drug delivery system and the one or more computing devices. Additional embodiments are possible according to the disclosure.

For example, a non-limiting matrix of state and identity information may include the following:

Condition State Information:
Temperature
Shock or vibration exposure
Light exposure
Color and/or turbidity (as relates to the drug)
Orientation
Geographic position
Temporal information
Operational State Information:
Device removed from package
Device removed from cold storage (e.g., refrigerator)
Device/drug temperature ready for administration
Delivery triggered
Device applied to patient
Device applied at correct location/orientation on patient
Cannula inserted into patient and/or inserted into correct tissue
Delivery in progress
Delivery complete
Error has occurred
Device Identity Information:
Drug name or identification, concentration, and/or amount
Security and/or anti-counterfeiting information
Patient prescription/therapeutic regime
Patient Identity Information:
Point of Care diagnostics on patient
Self-analyzed measure of progress
Fingerprint, pin, or other secure identification information This information may be used to control the drug delivery system or device, to be communicated to other computing devices, or otherwise to be used, and an exemplary listing of certain additional uses is included below. The listing and additional comments below is not intended to supersede, but to augment the discussion above, and is intended to be non-limiting.

As one example, the drug delivery system or the one or more computing devices may make a determination regarding the authenticity of the drug and its compliance with manufacturing standards. Such a determination may be made by the drug delivery device at block 208 of method 200, for example. The determination may be made based on the temperature, shock or vibration exposure, and/or light exposure of the drug delivery device/drug (or a history of one or more of these conditions) and color and/or turbidity of the drug (as determined by an optical inspection). This determination may result in control of the drug delivery device to either lock or unlock the device, according to the determination made. See blocks 206-412 and 218, 224 of the method 200.

As another example, the drug delivery system or the one or more computing devices may make a determination whether the drug is appropriate for the patient. See block 206-212 of method 200. The determination may be made based on one or more of the items of device of patient identify information listed above, and may also result in control of the drug delivery device to either lock or unlock the device, according to the determination made. See blocks 206-212 and 218, 224 of method 200.

As a further example, the drug delivery system or the one or more computing devices may make a determination whether the dose has been correctly administered. This determination may be carried out after determining that the drug is appropriate for the patient and/or that the drug is authentic (e.g., not counterfeit) and is in compliance with manufacturing standards. See the preceding paragraphs. The determination whether the dose has been correctly administered may depend on one or more of the types of operational state information listed above. This information may be used to update the patient record, determine the patient compliance or therapy progress, and may prompt communication with the pharmacy regarding a refill, or with the payer (e.g., insurance company) to authorize payment for the drug delivery device. See blocks 204-214 of method 200, and servers 142, 144 of FIG. 1.

As a further alternative, the drug delivery system or the one or more computing devices may use the information to make a determination regarding the operational state of the drug delivery device, and to generate instructional messages to guide the user through the actions required for the proper use of the drug delivery device. The determination may be based on any of the operational state information listed above, and the instructions generated may be dictated by the actions that need to be performed after the operational state that has just occurred. Implementation of interactive instructions that follow the changing states of the drug delivery device may help the user have confidence in administration of the drug.

As a further alternative, the drug delivery system or the one or more computing devices may use the information to make a determination that other people nearby are taking the same medication. See blocks 206-212 of method 200. This determination may be made based on the drug identity information and the patient identity information, in combination with the drug delivery system geographic location information. This determination may prompt a communication with the patient (see blocks 216, 222 of method 200) regarding local support networks of persons with similar conditions and/or taking similar drugs or medication to permit the patient to receive support and encouragement from such networks. Alternatively, the determination may prompt a communication with the local support network(s) (see blocks 214, 220 of method 200) to provide support and encouragement to the patient. As s further alternative, the determination may prompt a personalized intervention communication to be sent to the patient (again, see blocks 216, 222 of method 200).

As a further alternative, the drug delivery system or the one or more computing devices may use the information to make a determination whether the patient is not in compliance with their therapy regime. See blocks 206-212 of method 200. The determination may be based in part on the drug identification information, such as the prescribed treatment regime, in part on condition state information, such as the passage of time, and in part on the operational state information, such as where the drug delivery device is removed from the packaging but where no additional operational state information is determined, reported or received during the passage of time from the removal from packaging operational state. Based on this information, the drug delivery system and/or the one or more computing devices may determine that an interaction with the patient should be generated, such as an alert may be displayed or sent to patient. See blocks 216, 222 of method 200. Furthermore, the drug delivery system and/or one or more computing devices may determine that a communication should be generated to be displayed or sent to a healthcare provider, caregiver, support giver and/or payer to encourage adherence to regime. See blocks 214, 220 of method 200.

As a further alternative, the drug delivery system or the one or more computing devices may use the information to make a determination that the patient needs more medication (a refill). See blocks 206-212 of method 200. The determination may be based in part on the drug identity information, such as the prescribed treatment regime, and in part on the operational state information, such as where the drug delivery has been completed. Based on this information, the one or more computing devices may generate a communication that is sent to the payer and/or pharmacy to request a prescription refill. See blocks 214, 220 of method 200.

As a further alternative, the drug delivery system or the one or more computing devices may use the information to make a determination that the injection was not performed correctly. See blocks 206-212 of method 200. The determination may be based in part on operational state information, in comparison with information that may be collected and stored regarding conventional norms in operation. Alternatively or additionally, a comparison between the determined, reported or received operational states may permit a determination to be made that the injection was not performed correctly. For example, the determination, reporting or receipt of operational state information indicating that the drug delivery is complete without operation state information indicating that device was triggered, that the device was applied to the patient, and/or that the cannula was inserted may indicate that the drug delivery device has failed to perform correctly, is faulty or was operated incorrectly.

As a further alternative, the drug delivery system or the one or more computing devices may use the information to make a determination that patient's condition is improving. The determination may be based in part on patient identity information, such as point-of-care diagnostics performed on the patient (e.g., blood glucose test or other testing) or self-analysis reporting, and in part on the determination, reporting or receipt of operational state information, such as where the drug delivery has been completed. The determination may rely upon an overall trend as opposed to individual determinations or reports, as it is believed that data or reporting trends are usually more indicative of improvement in a patient's condition than the patient's condition as determined at individual instances for serious diseases. As such, the information gathered regarding the patient and the operational state of the drug delivery system/device may be combined with combined with therapy compliance history. This determination may result in individualized interventions to be generated, which interventions (such as encouraging messages and other forms of positive reinforcement) may increase persistence in therapy.

As a further alternative, the drug delivery system or the one or more computing devices may use the information to make a determination of the time of day (or week, month, etc.) that the patient usually takes their medication. This determination may be based, in part, on the patient record in which time information is associated with operational state information, such as relates to the triggering of the drug delivery device or the completion of the drug delivery. This determination may also rely on device identity information, such as the prescribed treatment regime. Based on this determination, the one or more computing devices may generate a reminder communication that is sent, for example, to the mobile device 110 to alert the patient that the time is approaching for them to administer their next dose. As the usefulness of reminders is enhanced when there is reasonable access to the drug delivery device and an opportunity for its use, it is beneficial to reinforce a patient's decision to take their medication at a particular time during the day, week, month, etc. Based on this determination, the one or more computing devices may also generate a personalized intervention, such as a message of encouragement to be used as a positive reinforcement.

As a further alternative, the drug delivery system or the one or more computing devices may use the information to make a determination where the patient usually takes their medication. This determination may be based, in part, on the patient record in which geographic position information is associated with operational state information, such as relates to the triggering of the drug delivery device or the completion of the drug delivery. This determination may also rely on device identity information, such as the prescribed treatment regime. Based on this determination, the one or more computing devices may generate a reminder communication that is sent, for example, to the mobile device 110 to alert the patient that the time is approaching for them to administer their next dose when they are at or near the geographic location where the patient usually uses the drug delivery system. As the usefulness of reminders is enhanced when there is reasonable access to the drug delivery device and an opportunity for its use, it is beneficial to reinforce a patient's decision to take their medication when they are in the usual location where they take their medication. Based on this determination, the one or more computing devices may also generate a personalized intervention, such as a message of encouragement to be used as a positive reinforcement.

Of course, the determinations regarding the usual time and location of the use of the drug delivery device may be combined, and the one or more computing devices may generate a message only when the patient or user is at or near their usual location of use at or near the time they usually use the drug delivery device.

While the foregoing has focused principally on the determinations made by the drug delivery system and/or one or more computing devices concerning the patient or the patient's use of the drug delivery device, determinations may be made with reference to the drug delivery device or the drug before the drug delivery device is made available to the patient or user.

For example, the drug delivery system or the one or more computing devices may use the information to make a determination whether delivery of a certain number of doses of a particular drug has arrived (e.g., instances of a drug delivery device containing the particular drug), for example, at a particular distributor or pharmacy location. This determination may be made based in part on the geographic location information and in part on the drug identify information. Based on this information, the one or more computing devices may generate a communication that is sent to the pharmacy or distributor (via the pharmacy or distributor server, for example) to inform them of the delivery of the drug delivery device. The pharmacy or distributor may use such a smart drug delivery device to simplify their logistics and inventory systems, for example.

Along similar lines, the drug delivery system or the one or more computing devices may use the information to make a determination that one or more of the drug delivery devices have been damaged en route to a particular distributor or pharmacy location. The determination may be made based in part on the geographic location information and in part on the drug identify information. The determination may also be based in part on condition state information, such as the temperature, shock/vibration exposure, light exposure or color and/or turbidity of the drug, whether determined at a particular time or over a period of time (i.e., a history as established in the drug delivery device record or the drug record). The determination may also or instead be based in part on the age of the product relative to its manufacture date or expiration date. The determination may also or instead be based in part on operational state information, such as the removal of a sterility barrier from the second end of the cannula of the drug delivery device. Based on this information, the one or more computing devices may generate a communication that is sent to the pharmacy or distributor (via the pharmacy or distributor server, for example) to inform them that the drug delivery device has been damaged or expired. The pharmacy or distributor may use such a smart drug delivery device to expedite the distributor's or the pharmacy's replacement of the damaged or expired product and prevent delays in patient therapy, for example.

As a further alternative, the drug delivery system or the one or more computing devices may use the information to make a determination that the product is as stated and has not been counterfeited. Such a determination may be based on the drug identity information, such as the name, concentration and amount of the product and the security and anti-counterfeiting measures associated with the drug. The determination made by the one or more computing devices may cause a communication to be generated, which communication may be transmitted to a governmental agency (e.g., customs/immigration officials) via the governmental agency server, to distributors and/or pharmacies via their respective servers, and/or patients and caregivers via their personal mobile devices.

As still further alternatives, certain determinations made by drug delivery systems and/or one or more computing devices operating according to embodiments of the disclosure may be used to control the drug delivery device remotely (i.e., without the controlling device being present in the same geographic location (e.g., room, building, or city) as the drug delivery device).

For example, the drug delivery system or the one or more computing devices may use the information to make a determination that the device needs to be controlled to prevent accidental operation. The determination may be based in part on the drug identity information in combination with, for example, certain patient identity information, such as biometric information in the form of a fingerprint. If it is determined that a party that is not authorized to use the drug delivery device is attempting to use the drug delivery device, then the one or more computing devices may generate a signal to be sent to the drug delivery system to lock the drug delivery device or to keep it locked until the drug delivery system is accessed by the patient or user for which it is intended.

As a further alternative, the drug delivery system or the one or more computing devices may use the information to make a determination that the patient associated with the drug delivery device is in a particular group or subgroup of patients or users that require or prefer a particular mode of operation for the drug delivery device. This determination may be made in part using information regarding the identity of the patient and the drug. Based on this determination, the drug delivery system and/or the one or more computing devices may generate a signal that customizes the operation of the drug delivery device. For example, the drug delivery device may be customized as to the sounds and/or lights used to alert the patient to various condition or operational states according to the specific market segment or patient population associated with the patient. As one example, different sounds may be used with pediatric patients than adult patients, louder sounds may be used with patients with hearing loss, and different lights or light sequences may be used with color-blind patients. Such control of the drug delivery device through the drug delivery system and/or one or more computing devices may reduce costs for drug delivery by permitting a single drug delivery device to be used that adapts to patient via software, rather than to use a plurality of different drug delivery device types, each of which has different hardware from the other types of drug delivery devices.

As a further alternative, the drug delivery system or the one or more computing devices may use the information to make a determination that the drug delivery device has not performed properly, and to generate a communication in that regard to the manufacture of the drug delivery device. The manufacturer may then determine modifications and/or improvements to enable proper administration of drug and can implement checks for sensed information and relay errors if it is not followed or is not successful. As has been mentioned above, the drug delivery system and/or one or more computing devices in communication with the drug delivery system need not be adapted or programmed to carry out every action listed in FIG. 2.

Figure 3:
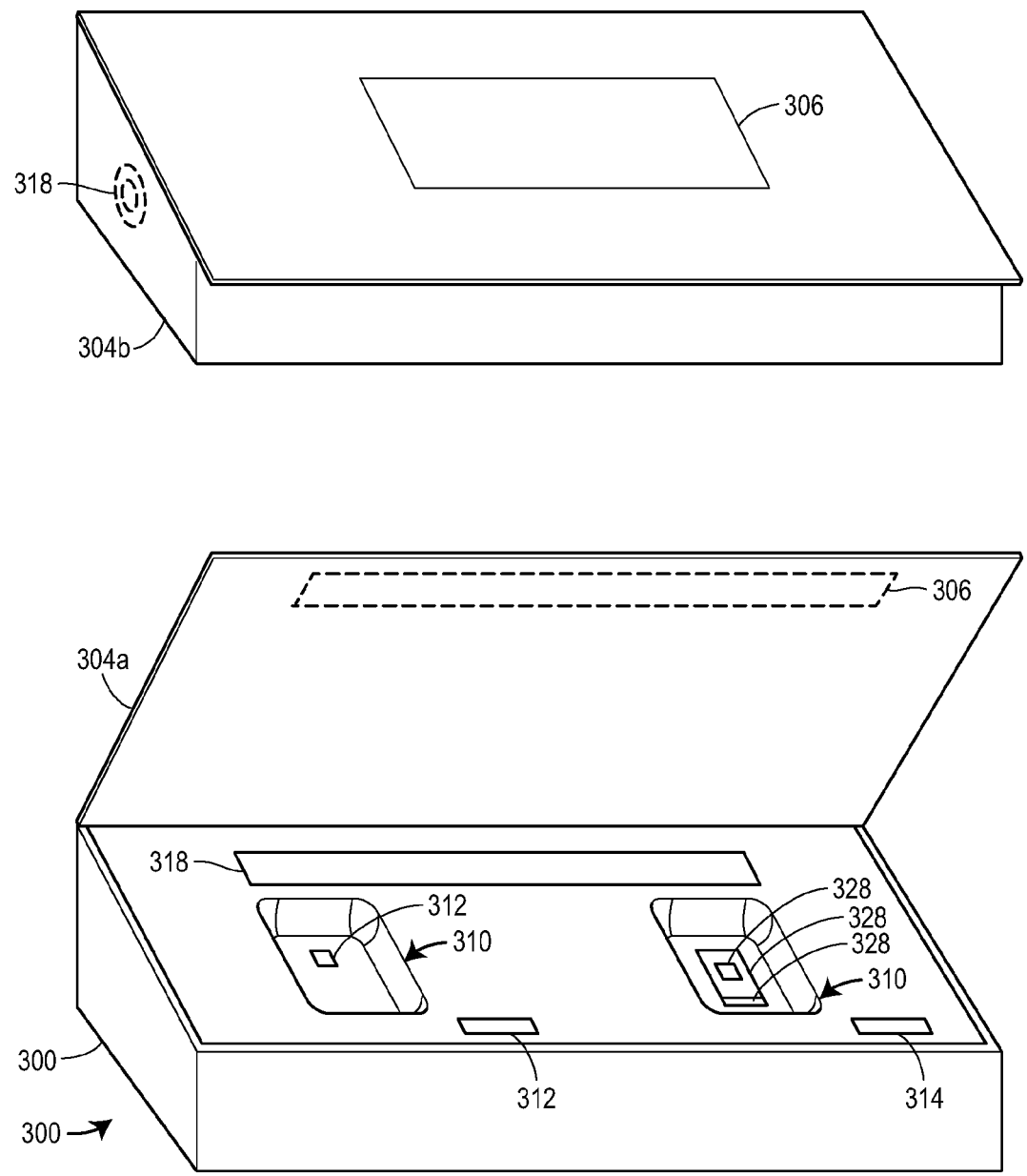
FIG. 3 comprises an illustration of a drug delivery system in accordance with various embodiments of the invention.

Referring now to FIG. 3, a drug delivery system 300 is provided which includes a storage container 302 defining at least one storage compartment 310 disposed within the storage container 302, a controller 314 having a processor, memory, and computer-executable instructions and/or logic, a container condition change mechanism 318, a drug delivery device 320, and a delivery device condition change mechanism 328. The system 300 may further include a sealing device such as a lid 304a and/or 304b, a communication device 306, a container sensor 312, and a delivery device sensor 322.

Figure 5:
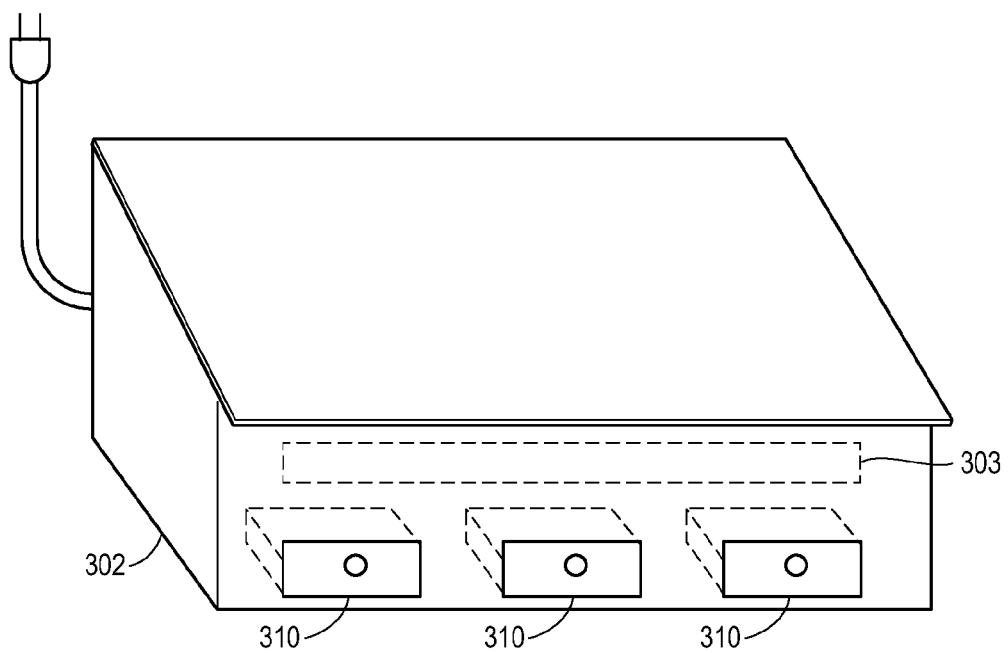
FIG. 5 comprises an illustration of an alternate drug delivery system having multiple compartments and/or drawers for storage of a number of drug delivery devices in accordance with various embodiments of the invention.

The storage container 302 may be constructed of any number of materials ranging from paper-based materials, polymers or other plastics, metals, and/or any combination of the same. The storage container 302 may define a cavity or cavities, or may be a solid, non-hollow configuration, or may have any combination of hollow and solid portions. The sealable storage compartment 310 may be configured in a number of ways such as a recessed area disposed on a surface of the storage container 302, a drawer-based system (such as illustrated in FIG. 5), a sealed package, box, and/or pouch, and the like. This storage container may facilitate rapid and non-degrading temperature adjustment of the drug delivery device 320 disposed therein. The storage compartment 310 many include any number of devices such as screens, vents, and the like to manage airflow to a cavity therein. Other examples are possible. The lid 304 may similarly be configured in a number of ways, for example, a hinged flap or door and/or a removable portion may be utilized. In some examples, the lid 304 assists in sealing the storage compartment 310. As illustrated in FIG. 5, the storage container 302 may also include storage 303 for additional supplies such as wipes, reusable drug delivery devices, instruction manuals, and the like, and the storage compartment 310 may include rechargeable power stations to recharge any number of drug delivery devices 320.

The communication device 306 may include any number of devices configured to communicate information. In some examples, the communication device 306 may include any number of displays, illumination devices, audio emitters, haptic feedback devices, and the like. Other examples are possible. The communication device 306 may be disposed on or near any portion of the storage container 302 such as on any surface, on an edge of the storage container 302, and the like. The storage container 302 may also include any number of additional components, such as, for example, a temperature adjustment devices and the like.

The container sensor 312 may be any type of sensor adapted to sense a condition of the storage container 302, and may be disposed in any number of locations relative to the storage container 302, such as, for example, within and/or near the sealable storage compartment 310, near a portion in close proximity to the lid 304, and the like. Other examples are possible. The container sensor or sensors 312 may be active and/or passive sensors such as infrared sensors, switches, circuits, and the like. In some approaches, a portion of a sensor may be removed upon removing the lid 304 and/or other components.

The container sensor 312 is adapted to communicate via any number of communication protocols, for example wired (e.g., via serial, USB, CAT-5, CAT-6, and the like), wireless (e.g., via Wi-Fi, RFID, NFC, Zigbee, Bluetooth, and the like) protocols. It is understood that any number of sealable storage compartments 310, container sensors 312, and/or lids 304 may be used.

The container sensor 312 may be any type of sensor suitable to sense a condition of the storage container 302. In many examples, the container sensor 312 may be a proximity sensor for sensing a presence of the drug delivery device 320 and/or whether the storage container 302 is in an open configuration (e.g. the lid 304 is removed or open). The container sensor 312 may also be a pressure sensor conductive switch for sensing whether the drug delivery device 320 is disposed within the storage container 302. In some examples, the container sensor 312 may sense a condition by experiencing a change in pressure. In these examples placing or removing an object from a location proximal to the container sensor 312 may cause a condition to be sensed. In other examples, a number of conductive connections may be provided, and upon moving a component within the device 300, electrical contacts may become engage or shorted, resulting in a changed sensed condition. In other approaches, the container sensor 312 may simply be a thermometer having designations for suitable temperature ranges. Other examples of sensors are possible.

The container condition change mechanism 318 may be any number of components, devices, and the like adapted to change a condition of the container. In some examples, the container condition change mechanism 318 may include a heating and/or a cooling mechanism adapted to raise and/or lower the temperature of the one or more storage compartments. For example, a number of fans, refrigeration units, heating coils, vents, and the like may be used. Other examples are possible. The container condition change mechanism 318 may also include a locking mechanism adapted to selectively restrict and permit access to the one or more storage compartments, and/or a communication device (e.g., communication device 306) adapted to communicate information relating to the drug delivery system. Further, the container condition change mechanism 318 may include a vacuum pump mechanism adapted to draw a vacuum on one or more of the one or more storage compartments 310 and/or a lock mechanism associated with selectively enabling access to one or more of the storage compartments 310. Other examples are possible.

The drug delivery device 320 is adapted to deliver a drug to a user. In some examples, the drug delivery device 320 may be any one of the previously-described delivery devices such as an injector, on-body injector, autoinjector, and the like, however, it is understood that any device capable of administering a drug to a patient may be used. In many examples (and as illustrated in FIG. 9) the drug delivery device 320 may include a reservoir, a delivery cannula having a proximal end in fluid communication with the reservoir and a distal end to be received within a patient, and a controllable element.

Figure 9:
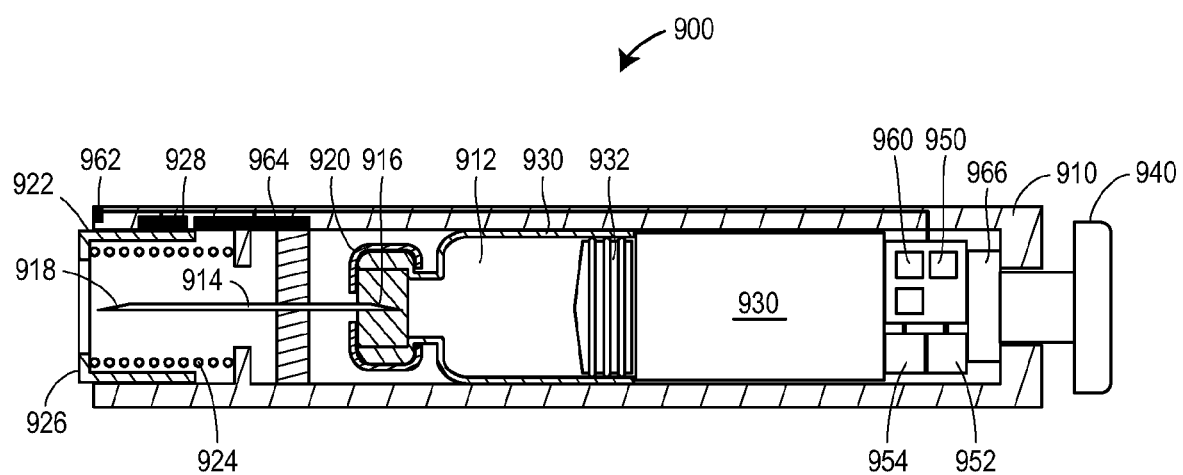
FIG. 9 comprises a cross-sectional view of an exemplary drug delivery device system including an autoinjector in accordance with various embodiments of the invention.

Turning briefly to FIG. 9, an exemplary drug delivery device 900 is described. It is understood that any of the components and/or features of drug delivery device 900 may be incorporated into the drug delivery devices described herein such as, for example, drug delivery device 320. The drug delivery device 900 may include a reservoir 912 and a cannula 914 having a first end 916 that may be connected or connectable in fluid communication to the reservoir 912 and a second end 918 that may be inserted into a patient. The cannula 914 may be, for example, a rigid needle having a beveled edge that may be sized such that the second end 918 of the cannula 914 is received under the skin so as to deliver a subcutaneous injection of the drug within the reservoir 912. The first end 916 of the cannula 914 may be disposed through a wall 920 of the reservoir 912, and thus be connected in fluid communication with the reservoir 912. As illustrated, the first end 916 of the cannula 914 may be disposed only partially through the wall 920 (which wall 920 may be a resealable septum or stopper, for example) such that the first end of the cannula 914 may not be connected in fluid communication until the second end 918 of the cannula 914 is inserted into the patient. In such a circumstance, the first end 916 of the cannula 914 may thus be described as connectable in fluid communication with the reservoir 912, although it will be recognized that there are other mechanisms by which the first end 916 of the cannula 914 may be connectable, but not connected, in fluid communication with the reservoir 912.

The drug delivery device 900 includes a shield 922 that may be deployed at least after the injection has been completed to limit access to the second end 918 of the cannula 914. According to certain embodiments, the shield 922 may have a biasing element 924 (such as a spring) that extends the shield 922 from the housing 910 such that a distal end 926 of the shield 922 extends beyond the second end 918 of the cannula 914 except when the shield 922 is disposed against the skin and the injection of the cannula 914 is actuated. In fact, the injection of the cannula 914 may be actuated according to certain embodiments of the autoinjector 900 by disposing the distal end 926 of the shield on or against the skin of the patient. The autoinjector 900 may also include a lock 928 that is associated with the shield 922 and which limits the movement of the shield 922 relative to the housing 910 of the autoinjector 900 such that the distal end 926 of the shield 922 extends from the housing 910 a sufficient distance to limit or prevent contact with the second end 918 of the cannula 914 after the cannula 914 has been removed from the skin of the patient after the drug has been delivered.

The drug delivery device 900 also includes at least one drive 930 that may be used to insert the second end 918 of the cannula 914 into the skin of the patient, and to inject the drug or medicament from the reservoir 912 through the cannula 914 into the patient. The drive 930 may include one or more springs, according to certain embodiments. According to other embodiments, the drive 930 may include a source of pressurized gas or a source of a material that undergoes a phase change, such that the escaping gas or phase changing material provides a motive force that may be applied to the reservoir 912 to eject the drug therefrom. According to still other embodiments, the drive 930 may include an electromechanical system, such as may include a motor for example, although such an electromechanical system may be more appropriate for the on-body autoinjector or infuser described in greater detail below. Other embodiments for the drive 930 will be recognized.

The drive 930 may cooperate with a wall 932 of the reservoir 922 to move that wall 932 toward the patient's skin. In accordance with such an embodiment, the wall 932 may be a stopper that is received within a bore 934, and which may move along the bore 934 from a first end to a second end to inject the drug from the reservoir 912. The drive 930 may also cooperate with the stopper 932 and/or the bore 934 to move the reservoir 912 relative to the housing 910 so as to move the second end 918 of the cannula 914 relative to the housing 910 and into the patient. According to those embodiments wherein the drive 930 cooperates with the stopper 932, this may occur before the first end 916 of the cannula 914 is in fluid communication with the reservoir 912. According to those embodiments wherein the drive cooperates with the bore 934, the drive may include one component (e.g., first spring) that cooperates with the bore 934 to move the reservoir 912 and cannula 914 relative to the housing 910, and a second component (e.g., second spring) that cooperates with the stopper 932 to move the stopper 932 relative to the bore 934.

The drive 930 is associated with an actuator 940. The actuator 940 activates the drive to cause the drive 930 to insert the cannula 914 and inject the drug from the reservoir 912 through the cannula 914 into the patient. The actuator 940 may, according to certain embodiments, be the shield 922. According to other embodiments, such as the embodiment illustrated, the actuator 940 may be a button that may be depressed by the user once the autoinjector 900 is disposed on or against the patient's skin. While the embodiment illustrated in FIG. 9 has the actuator 940 disposed at one end of the device, the actuator 940 could be disposed on the side of the device as well. As illustrated, the reservoir 912, biasing element 924, lock 928, and the drive 930 are disposed within the housing 910, along with at least part of the cannula 914.

Referring again to FIG. 3, the drug delivery device 320 may also include a delivery device sensor 322 coupled thereto. The drug delivery device 320 is adapted to be at least partially disposed within the sealable storage compartment 310. The delivery device sensor 322 is adapted communicate via any number of communication protocols, for example wired (e.g., via serial, USB, CAT-5, CAT-6, and the like), wireless (e.g., via Wi-Fi, RFID, NFC, Zigbee, Bluetooth, and the like) protocols. It is understood that any number of drug delivery devices 320 may be used, and that any number of delivery device sensors 322 may be coupled to these drug delivery devices 320. As with the container sensor 312, the drug delivery device sensor 322 may be any type of sensor suitable to sense a condition of the drug delivery device 320 such as, for example, a thermometer or any other type of temperature sensor for sensing a temperature of a drug stored in a reservoir of the drug delivery device 320 (and may designations for suitable temperature ranges of the drug delivery device 320), a switch for detecting the position of a locking mechanism associated with an actuator of the drug delivery device, a switch for detecting the position of a plunger mechanism associated with an actuator of the drug delivery device, a switch for detecting the position of a needle cap on the drug delivery device, a photo sensor for detecting at least one of an opacity and a color of a drug stored in a reservoir of the drug delivery device, and the like. Other examples are possible.

As with the container condition change mechanism 328, the delivery device condition change mechanism may include any number of components, devices, and the like adapted to change a condition of the drug delivery device 320. In some examples, the container condition change mechanism 328 may include a locking mechanism adapted to selectively enable use of the drug delivery device 320, a heating and/or cooling mechanism adapted to raise and/or lower the temperature of at least a portion of the drug delivery device 320, a communication device adapted to communicate information relating to the drug delivery system, and the like. Other examples are possible.

The controller 314 is coupled to the storage container 310 and may be any number of electrical and/or electro-mechanical devices. For example, the controller 314 may consist of any number of hardware and/or software elements such as memories, processors, and computer-executable instructions stored on the memory adapted to execute a task and/or effect an action. It is understood that any number of controllers 314 may be used in conjunction with the system 300. The controller 314 is adapted to communicate via any number of communication protocols, for example wired, wireless (e.g., RFID, NFC, Bluetooth, and the like) protocols. The controller 314 may further include any number of processors or processing elements which may process and execute calculations and/or tasks.

In operation, the container sensor 312 is adapted to sense a condition of the storage container 302 and the delivery device sensor 322 is adapted to sense a condition of the drug delivery device 320. The controller 314 is adapted to receive the sensed condition from the container sensor 312 and/or the delivery device sensor 322 and instruct at least one of the container condition change mechanism 318 to impart a change on one or more conditions of the storage compartments 310 and the delivery device condition change mechanism 328 to impart a change on one or more conditions of the drug delivery device 328.

As described previously, the sensed information may include any combination of operational state and/or condition state information. Accordingly, the container sensor or sensors 312 and/or the delivery device sensor or sensors 322 may include: proximity sensors adapted to detect the presence of the drug delivery device 320 within a sealable storage compartment 310, whether the storage container 302 is in an open or closed configuration (e.g., the lid 304 is open or removed), and/or whether the storage container 302 is in a sealed or unsealed configuration; temperature sensors located inside and/or outside of the storage container 302 adapted to determine internal temperatures of the storage compartment and/or the drug delivery device 320 and external, ambient temperatures of the storage container 302; pressure-sensitive conductive switch sensors triggered upon device removal, superelastic materials adapted to engage a circuit when certain characteristics of the storage container 302 are met; humidity sensors for sensing a humidity within any number of compartments 310 of the storage container 302, and the like. The temperature sensors may additionally be used to detect a temperature differential between the ambient temperature and the internal temperature. In yet other approaches, the container sensor(s) 312 and/or the delivery device sensor(s) 322 may be adapted to detect a quantity of drug or medicant contained within the drug delivery device 320 in the event the drug delivery device 320 contains multiple doses. Other examples are possible.

The controller 314 may instruct the container condition change mechanism 318 to change temperature of the storage container 302, any number of sealable storage compartments 310, and/or any number of drug delivery devices 320. In these examples and as previously described, a temperature adjustment device such as a cooling and/or a heating device may be provided. A refrigerant-based cooling device may be used to lower the temperature to suitable storage levels of the drug delivery device 320. In some examples, the storage container may passively adjust the temperature via a ventilation system having any number of vents adapted to adjust the amount of ventilation received by the storage container 302. In some examples, an active device may be used such as an active convection unit which may include any number of fans that provide power to a venting system. Active heating may also be utilized to adjust the temperature, such as, for example, using reverse cooling elements to provide heat and/or resistive heating components such as tubes or mesh disposed in a path of typical air flow. Further, a number of heating coils or similar devices may be used to adjust the temperature. The system 300 may include any combination of these temperature adjustment devices, thus the controller 314 may be adapted to determine an appropriate combination to efficiently adjust the temperature.

The controller 314 may also instruct the container condition change mechanism 318 to alert a user of the sensed condition via the communication device 306. In one example, the communication device 306 may comprise a display or alarm which communicates a message that the drug delivery device 320 is or is not ready for use depending on the sensed information. The communication device 306 may also be adapted to display the quantity of drug delivery devices 320 remaining for use. The communication device 306 may communicate a message in any number of ways such as, for example, through words (e.g., "DEVICE READY FOR USE", "DEVICE NOT READY FOR USE", "DEVICE REMOVED FROM CONTAINER", and/or "DEVICE MALFUNCTION") which may include a countdown or timer, audible beeps or noises, and/or visual flashes. In many of these examples, the communication device 306 may transmit or display these messages based on a sensed temperature by one or both of the container sensor(s) 312 and the device sensor(s) 322.

As non-limiting examples, if the temperature of the drug delivery device 320 is greater than a threshold value (such as, for example, 10° C.) and the drug delivery device 320 or the storage container 302 is reporting an unopened condition, the communication device 306 may display an indication that the drug delivery device needs to be refrigerated. If the temperature of the drug delivery device 320 is greater than a threshold value (such as, for example, 10° C.) and the drug delivery device 320 or the storage container 302 is reporting an opened condition, the communication device 306 may display an indication that the drug delivery device will be ready for use in a specified period of time. If the temperature of the drug delivery device 320 is less than a threshold value (such as, for example, 10° C.), and the drug delivery device 320 or the storage container 302 is reporting a closed condition (meaning the drug delivery device is disposed within the storage compartment 302), the communication device 306 may display an indication that the drug delivery device is in a low-power mode in which the controller 314 causes the device 300 to use a reduced amount of energy during operation.

In other examples, the container sensor 312 and/or the delivery device sensor 322 performs a temperature check in the form of an evaluation of the temperature history of the drug product to determine the range and duration of temperatures experienced by the drug product in the past (e.g., during storage, distribution, etc.). If the temperature history of the drug product is unacceptable due to, for example, the drug product being exposed to elevated temperatures for several days during shipment, the controller 314 may lockout the drug delivery device 320 so that it cannot be used to deliver the drug product to a patient, and additionally, may control the other components (e.g., a communication module) to generate and transmit a report to a computing device representative of the unacceptability of drug product's temperature history. In some embodiments, upon a determination that the temperature of the drug product exceeds a threshold temperature, the controller may begin a timer that runs until the temperature falls back below the threshold temperature. If the duration of the timer exceeds a predefined time limit, the controller 314 may lockout the drug delivery device 320 and control a communication module to transmit a report representative of the unacceptability of drug product's temperature history.

It is understood that any number of the previously described sensors may use their sensed data to determine whether the drug delivery device 320 should be locked to restrict access thereto. For example, a photo sensor may compare the opacity of the drug stored in the reservoir of the drug delivery device with a database of acceptable opacity ranges and determine whether the present opacity of the drug is acceptable. If it is determined that the drug is not acceptable for use, the controller 314 may again lockout the drug delivery device 320. Other examples are possible.

The communication device 306 may include any number of illumination elements which change colors and/or intensity when a sensed condition is met (e.g., red when the drug delivery device 320 is not ready for use and green when the drug delivery device 320 is ready for use). Further, the communication device 306 may provide instructions or details for administering the drug via the drug delivery device 320. Other examples are possible.

The controller 314 may also instruct the container condition change mechanism 318 to log the sensed condition by a computing device having a memory. In some approaches, the controller 314 may be adapted to log this information, and in other examples, the system 300 may include a remote computing device adapted to communicate with the controller (such as, for example, any of the computing devices 104, 110, 114, 140, 142, 144, 146, 148 AS described in FIG. 1). This logged information may be used in a number of ways, such as to generate a historical representation of a patient's usage profile, to provide incentives to the patient when a quantity of drug delivery devices 320 is depleting, to determine if the patient is properly utilizing the drug delivery device 320, to determine a temperature excursion of the drug delivery device 320, and the like. Manufacturers may also use this information to their benefit to obtain a better understanding of the drug and drug delivery device 320. Other examples are possible.

The controller 314 may also instruct the container condition change mechanism 318 to present information regarding the sensed condition to a user via a device such as the communication device 306. For example, the controller 314 may be adapted to cause the communication device 306 to display the current temperature of the drug delivery device 320 and/or the number of remaining drug delivery devices. Other examples relating to the use and administration of the drug delivery device 320 are possible.

The controller 314 may also instruct the container condition change mechanism 318 to calculate an approximate time until the drug delivery device 320 will be suitable for use (e.g., how long until the drug delivery device 320 reaches a threshold temperature appropriate for administering the drug). The controller 314 may be coupled to a processing device and a memory device which includes data and/or trends relating to temperature increases and/or decreases. As such, the controller 314 may calculate, based on the current temperature of the drug delivery device, an approximate time until the drug delivery device 320 will reach the desired temperature. The controller 314 may further be adapted to present this information via the communication device 306.

In some examples where multiple storage compartments 310 are disposed within the storage container 302, each storage compartment 310 may be sealable and may be thermally isolated from the remaining storage compartments 310. The storage container 302 and/or particular sealable storage compartments 310 may be vacuum sealed and pumped to create this thermally isolated area within the storage container 302. Other methods of thermally sealing the storage compartments 310 are possible. The storage compartments may also be hermetically sealed. Alternatively, any number of storage compartments 310 may be "thermally coupled" or in thermal communication with each other, while other storage compartments 310 or groups thereof may remain thermally isolated. As such, the drug delivery devices 320 in these thermally isolated storage compartments 310 may also be thermally isolated from remaining drug delivery devices 320. The controller 314 may be adapted to selectively adjust the temperature of any combination of thermally isolated storage compartments 310 such that the temperature of the corresponding drug delivery device or devices 320 is adjusted in a selective manner.

As a non-limiting example, the controller 314 may receive data from one or both of the container sensor(s) 312 and the delivery device sensor(s) 322 regarding the expiration date of the drugs disposed within the storage container 302. The controller may receive and process this information and determine the appropriate drug delivery device 320 to selectively adjust the temperature of to allow the soonest-expiring drug delivery device 320 to be used first. In another example, the controller 314 may cause access to any number of sealable storage compartments 310 to be restricted via any type of locking mechanism, while allowing a particular sealable storage compartment to be opened. Other examples are possible.

It will be understood that any of the described actions may be performed in conjunction with each-other. For example, the controller 314 may be adapted to cause the storage container to change temperature and alert the user of the sensed condition while transmitting the sensed condition to a remote computing device. Other examples are possible.

Figure 8:
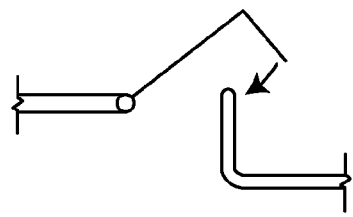
FIG. 8 comprises an illustration of an example container sensor of the drug delivery system of FIG. 3 constructed of a deformable superelastic material in accordance with various embodiments of the invention.

Turning briefly to FIG. 8, an example embodiment of a container sensor 312 is described. This container sensor 312 is constructed from a deformable superelastic material such as a shape-memory alloy which is adapted to "remember" an original shape and/or configuration and return to this configuration upon being heated. In some examples, the shape-memory alloy may be a nitinol wire. Other examples are possible. The superelastic material may be bent and heat treated to change from an extended to a relaxed configuration or vice versa at any range of temperatures, such as between 0° C. and 100°, or any range there between. The superelastic material may be used to short a power circuit and/or cause an electronic component to enter an "awoken" state in which the presence of drug delivery devices 320, temperatures, and other conditions are monitored and further create communication with the controller 314 and/or external devices. Alternatively, the superelastic material may cause a "sleep" state at a desired temperature range that causes components to enter a lower power state and thus reduce energy consumption. In some examples, the material may simply cause a container sensor 310 to inquire as to whether the storage container 302 is in an open or closed configuration. Other examples are possible.

Thus, in some examples, the container sensor 312 may be adapted to lose electrical contact with the circuit when it is above or below a threshold condition (e.g., a desired temperature), and return to an original shape which engages a circuit upon reaching the threshold condition. As such, the container sensor 312 may transmit the sensed condition that an area in which the container sensor 312 is disposed has reached a threshold value to the controller 314.

As previously mentioned, one or both of the container sensor 312 and the delivery device sensor 322 may communicate via RFID and/or other wireless transmission signals. For example, the container and/or delivery sensors 312, 322 may comprise RFID tags having information relating to the use of the drug being stored. As before, these sensors may be disposed at any location on and/or near the storage container 302 and drug delivery device 320.

As an illustrative example, a number of drug delivery devices 320 may have corresponding delivery device sensors 322 coupled thereto. The delivery device sensors 322 may in turn have information relating to the drug expiration date stored thereon. Upon a user requesting a drug delivery device 320 to be prepared for administration, the controller 314 may retrieve the information from a number of the drug delivery device sensors 322 and selectively cause the drug delivery device 320 having an earliest expiration date to be prepared for use (e.g., to be heated to a suitable temperature). The controller 314 may further cause the remaining drug delivery devices 320 to become temporarily inaccessible to ensure the correct drug delivery device is used. Further still, the controller 314 may cause the communication device 306 to indicate which particular drug delivery device 320 to use and when it will be ready for use. Other examples are available.

Figure 4:
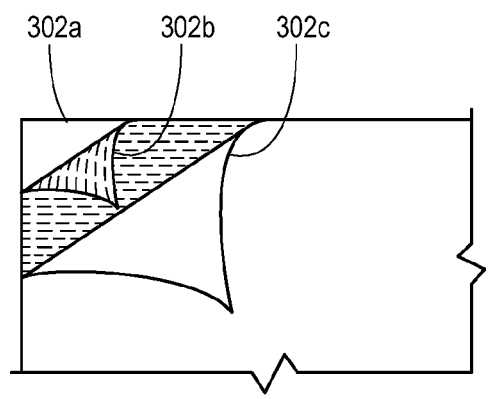
FIG. 4 comprises an illustration of a multi-layered surface of the drug delivery system of FIG. 3 adapted to restrict wireless transmissions in accordance with various embodiments of the invention.

In some of these examples, the storage container 302 may be constructed of a material which may impede the transmission of RF signals used with these RFID tags. As an example and as illustrated in FIG. 4, the storage container 302 may include a multi-layered material having outer layers 302a, 302c and an inner reflective layer 302b such as a metallic material. As such, the storage container may act as a "Faraday cage" when closed or sealed and may block wireless signals from escaping the storage compartment. Upon opening the storage compartment, the RFID device may resume communication with an external computing device (e.g., a remote computer or the cloud) to perform any number of tasks such as setting use timers and the like.

Figure 6:
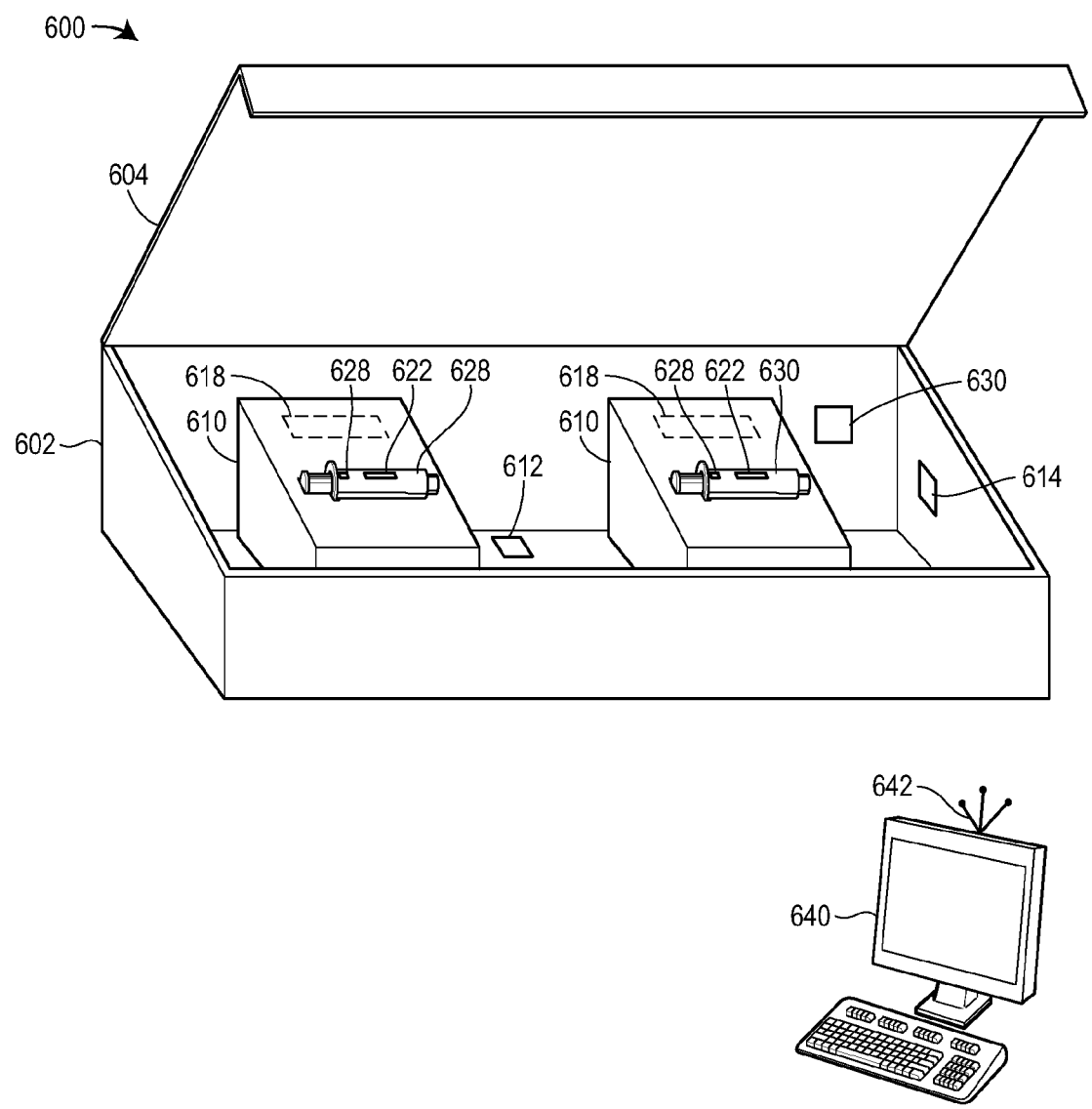
FIG. 6 comprises an illustration of an alternate drug delivery system having communication modules adapted to communicate with remote computing devices in accordance with various embodiments of the invention.

Referring now to FIG. 6, an alternate drug delivery system 600 is provided. It will be understood that reference characters having the same two-digit suffixes (e.g., storage container 602) represent previously described elements (e.g., storage container 302) and will not be discussed in substantial detail. It is further understood that any additional features described with regards to system 600 may be used in combination with any of the systems and embodiments described in this disclosure. Specifically, the system 600 may be viewed as at least a portion of the system illustrated in FIG. 1. In the alternate drug delivery system 600, a storage container 602 includes at least one storage container compartment 610, a storage container sensor 612 coupled to the storage container for sensing a condition of the storage container 602, a container condition change mechanism 618 coupled to the storage container 602 for imparting a change on the condition of the storage compartment or compartments 610, a drug delivery device 620 adapted to deliver a drug to a user and to be at least partially disposed within one or more of the storage compartments 610, at least one delivery device sensor 622 coupled to the drug delivery device 620, a delivery device condition change mechanism 628 coupled to the drug delivery device 620 for sensing a condition of the drug delivery device, a first communication module 630 coupled to the storage container 602, a computing device 640 remotely located (e.g., not part of the container or drug delivery device) having a second communication module 642 coupled thereto, and a controller 614 coupled to the first communication module 630. The computing device 640 may include a memory, a processor, and computer-executable instructions stored on the memory.

The controller 614 is adapted to communicate with the first communication module 630 via any number of wired and/or wireless communication protocols. Similarly, the first and second communication modules 630, 642 are adapted to communicate with each other via any number of wired and/or wireless communication protocols.

The computing device 640 may be any combination of hardware and software elements adapted to perform calculations and/or execute a task. In some examples, the computing device 640 may be a personal computer, a server, a cellular telephone, tablet, laptop, or any number of similar devices and can be considered to represent similar construction to the devices 110, 104, and 114 in FIG. 1.

In operation, the controller 614 is adapted to receive a signal representing a sensed condition from at least one of the storage container sensor 612 and the delivery device sensor 622 and cause the first communication module 630 to transmit a signal to the second communication module 642 of the computing device 640. The computing device 640 is then adapted to determine and transmit a corresponding signal to the first communication module 630 which is transmitted to the controller 614. The controller 614 then instructs the container condition change mechanism 618 to impart a change on the storage container 602 and/or instructs the delivery device condition change mechanism 628 to impart a change on the drug delivery device 620.

In some examples, the signal transmitted to the computing device 640 may include information relating to a temperature excursion experienced within the storage container 602, a frequency of use of the drug delivery device 620, the number of unused drug delivery devices 620 remaining in the storage container 602, and the like. By "temperature excursion" and as used herein, it is meant a deviation from given instructions in which a time temperature sensitive pharmaceutical product is exposed to temperatures outside the range(s) prescribed for storage and/or transport. The signal transmitted to the computing device 640 may include any type of information relating to the sensed data. The computing device 640 primarily uses this information to determine appropriate use conditions of the drug delivery device 620 and/or to simply be stored as historical data for future use by the user, manufacturer, and/or any other interested party. In some examples, the computing device 640 may also send this information relating to the sensed data to a cloud-based computing system (e.g., a data farm) for collecting the data. Other examples are possible.

In some examples, the storage container 602 is adapted to restrict the first communication module 630 from transmitting the signal to the computing device 640 when the storage container 602 is in a closed configuration as previously described with regards to FIGS. 3 and 4 by using a material such as a metallic foil to disrupt the transmission of signals. Accordingly, the storage container 602 may be placed in a low-power state when signal transmissions are restricted, and may be awoken to transmit signals upon opening the storage container 602.

Figure 7:
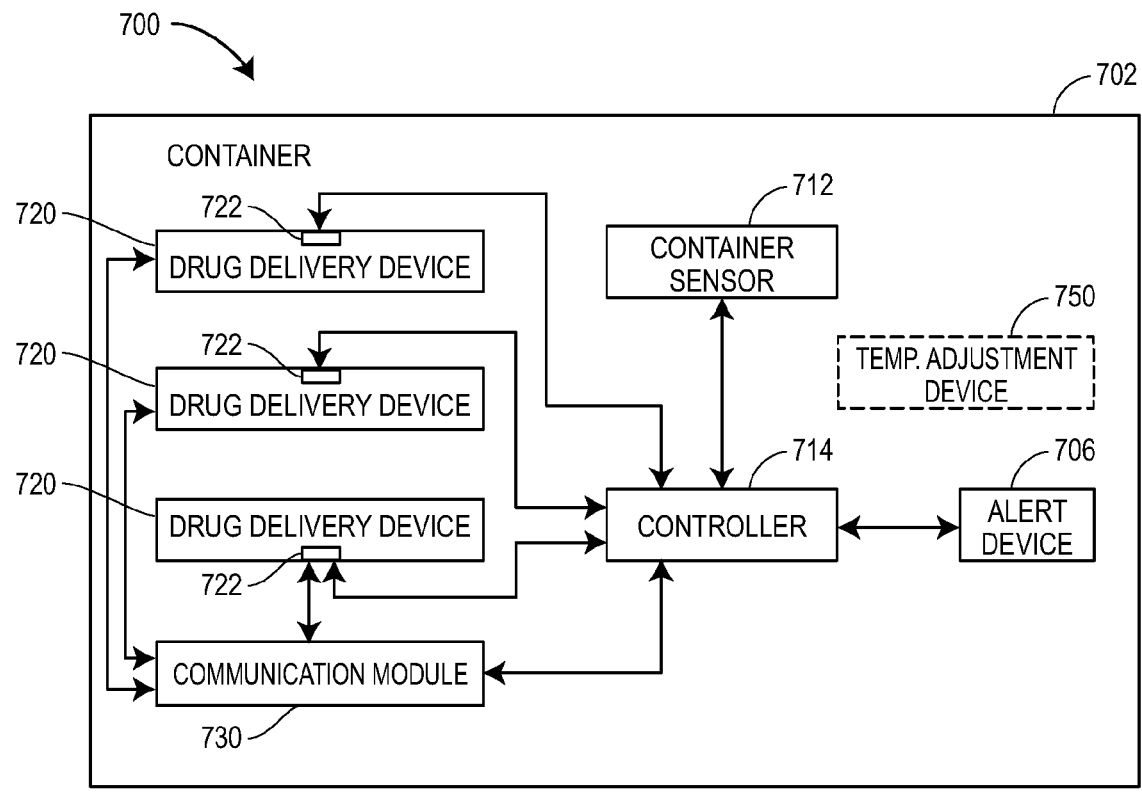
FIG. 7 comprises a block diagram of an alternate drug delivery system in accordance with various embodiments of the invention.

Referring now to FIG. 7, an alternate drug delivery system 700 is provided. It will be understood that reference characters having the same two-digit suffixes (e.g., storage container 702) represent previously described elements (e.g., storage container 302, 602) and will not be discussed in substantial detail. It is further understood that any additional features described with regards to system 700 may be used in combination with any of the systems described herein. In the alternate drug delivery system 700 is provided for selective storage of a plurality of drug delivery devices 720 each having at least one device sensor 722 and further selectively housing at least one communication module 730 for transmitting information collected by the device sensors 722. The storage container 702 may further include at least one container sensor being adapted to sense a condition of the container 702, a controller 714 coupled to the container sensor and the device sensor(s) 722, and an alert device 706 coupled to the controller 714.

The communication module 730 is adapted to communicate with any number of remote computing devices as previously described using any number of communications protocols such as, for example, wired or wireless communication protocols using any number of technologies. The alert device 706 may be any type of audio (such as a speaker), visual (such as a display or illumination device), haptic, or other device used to create an alert.

The controller 714 is adapted to receive a sensed condition and, upon the sensed condition reaching a threshold value, the controller 714 transmits a control command to the alert device 706 and/or the communication module 730 indicating the sensed condition has been met. This sensed condition may be conditional state information, operational state information, or any combination of conditional and operational state information. The state information may be communicated to any number of remote computing devices such as, for example, the computing devices previously described.

The container 702 may further include a container condition change mechanism 750 which receives a control command from the controller 714 and selectively changes a condition of any number of drug delivery devices 720. In the illustration of FIG. 7, the container condition change mechanism 750 is a temperature adjustment device which may adjust the temperature of any of the drug delivery devices 720.

In many of these approaches, a number of drug delivery devices stored in a number of compartments in a storage container are managed. Data may be obtained from each of the drug delivery devices using a controller. Based on this obtained data, a particular drug delivery device may be determined to effect an action upon. A container condition change mechanism and/or a drug delivery device condition change mechanism coupled to the container and/or the drug delivery device may then be instructed to impart a change on one or more conditions of the compartments and/or the drug delivery device or devices. The action may then be selectively effected on one of the compartments in which the particular drug delivery device is disposed.

In one example, this determination is made based on the expiration date of the drug delivery devices being stored in the container. That is, it may be determined that a drug delivery device having the earliest expiration date should be acted upon. This imparted change may include selectively adjusting a temperature of the compartment housing the particular drug delivery device, selectively providing access to one or any number of the compartments, displaying information relating to the sensed condition, providing a user with information relating to the drug delivery device or devices, logging the sensed condition, transmitting the sensed condition, and/or determining an appropriate time to use the drug delivery device. Other examples are possible.

Figure 10:
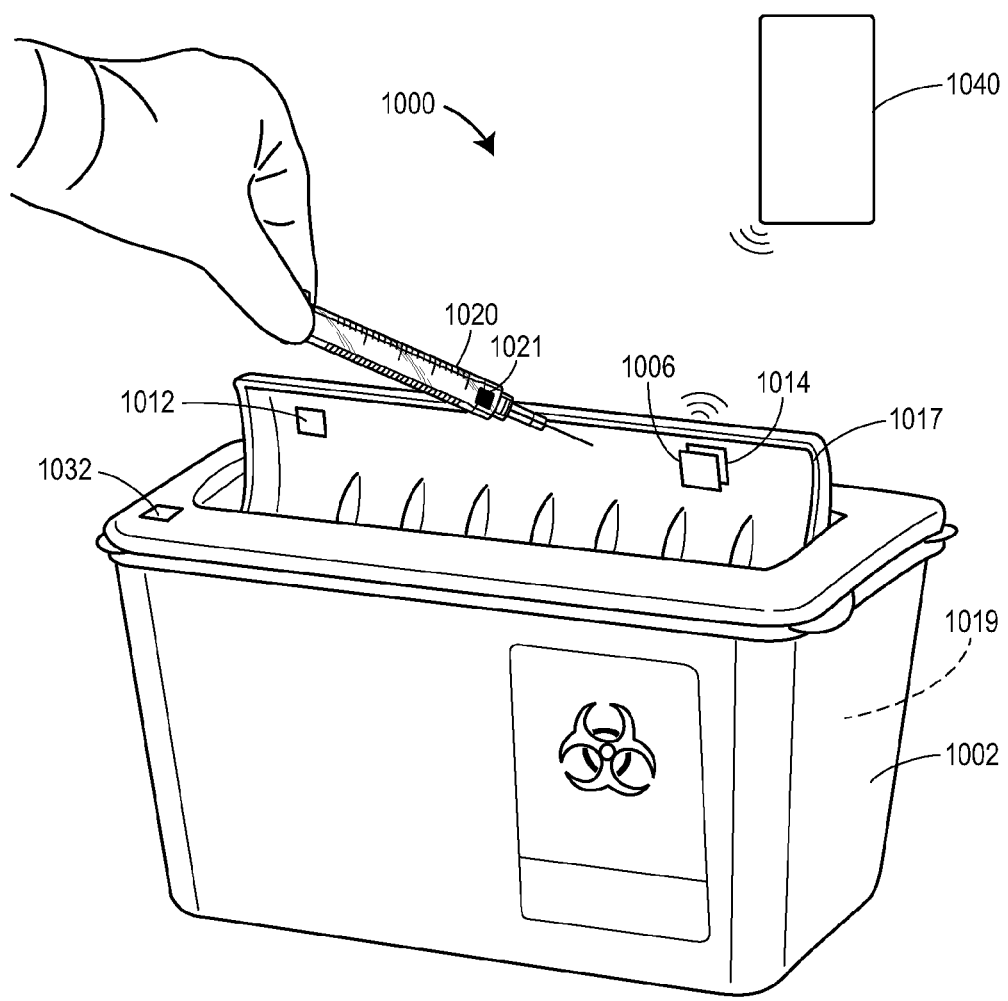
FIG. 10 comprises an illustration of an alternative drug delivery device storage system in accordance with various embodiments of the invention.

Referring now to FIG. 10, an alternate drug delivery device storage system 1000 is provided. It will be understood that reference characters having the same two-digit suffixes (e.g., storage container 1002) represent previously described elements (e.g., storage container 302) and will not be discussed in substantial detail. It is further understood that any additional features described with regards to system 1000 may be used in combination with any of the systems and embodiments described in this disclosure. Specifically, the system 1000 may be viewed as at least a portion of the system illustrated in FIG. 1.

The alternate drug delivery device storage system 1000 includes a storage container 1002 defining one or more storage compartments, at least one container sensor 1012 coupled to the storage container for sensing a condition of the container 1002, and a controller 1014 coupled to the storage container 1002. The controller 1014 includes a memory, a processor, and a communication module 1006. The controller 1014 is adapted to receive the sensed condition of the container 1002 and transmit a signal containing a representation of the sensed condition via the communication module 1006.

The container sensor 1012 may include an accelerometer mounted on a movable lid or door 1017 of the storage container 1002, and which is adapted to sense a movement of the movable lid or door of the storage container 1002. Other examples of the container sensor 1012 are possible and can include gyrometers, proximity sensors, switches, etc. The communication module 1006 may be adapted to transmit the sensed data to a remote computing device 1040, which may be at least one of a personal computing device, a remotely located server, a mobile communication device, and/or a tablet computer. In some forms, the storage system 1000 may include a coupling device 1032 which may communicatively couple the container sensor 1012 to the remote computing device 1040.

As an example, the storage container 1002 may be a container which is adapted to store and/or dispose of used drug delivery devices 1020 and may be located at a patient's residence and/or other location where drugs are commonly administered. After using the drug delivery device 1020, a user may place the drug delivery device 1020 in the one or more storage compartments 1019 by opening a portion of the storage container (e.g., a lid or door 1017) and subsequently closing the same portion. As illustrated in FIG. 10, the storage container 1002 opens and closes via a hinged, rotatable lid or door 1017. Other examples are possible. In some forms, the storage container 1002 may be secured in a number of methods so as to restrict access to the one or more storage compartments. In other words, the storage container 1002 may be adapted to accept drug delivery devices, but may be locked or secured to prevent access to drug delivery devices contained therein.

The at least one container sensor 1012 may be disposed on a portion of the lid or door 1017 and may be adapted to sense movement thereof and log the activity to the memory of the controller 1014. In other words, opening the lid or door 1017 may serve as a representation that the drug delivery device 1020 was used or administered, and accordingly this information may be of use by the user, caregivers, doctors, family members, and the like.

In some approaches, the coupling device 1032 may consist of a button that is pressed or toggled which may cause the container sensor 1012 to be coupled (e.g., paired) to the computing device 1040. In one example, the coupling device 1032 may be a pairing button adapted to communicate via a wireless protocol such as Bluetooth, and may be adapted to operate on low amounts of energy. Other examples are possible.

So configured, the drug delivery device storage system 1000 may allow for accurately tracking use of a patient's drug delivery devices 1020. The controller 1014 may send information relating to the use and/or disposal of the drug delivery devices to the remote computing device 1040 to process this information as appropriate.

In some examples, the drug delivery device 1020 may also include any number of sensors or informational tags 1021 which may be adapted to communicate with the container sensor 1012. The sensors or tags 1021 may relay information to the container sensor 1012 to provide a robust drug delivery device usage profile. For example, the drug delivery device sensor 1021 may include information of what particular drug was administered, its expiration date, environmental conditions, and any number of additional data relating to the drug delivery device including for example whether or not the drug was completely dispensed from the device or not. The drug delivery device sensor 1021 may communicate with the storage container sensor 1012 via any number of methods, including those described in the present description.

So configured, the approaches described herein may allow for near-autonomous preparation of drug delivery devices. A user may supply an initial amount of information, and the container may automatically determine which drug delivery device to selectively prepare for the user. The patient may set an initial schedule or queue for medication and be notified when it is ready for use. Alternatively, the container may automatically prepare the drug delivery device at a designated time such that the user simply removes one of the drug delivery devices and administers the drug without having to determine whether the drug is ready for use. Any number of sealable compartments may be thermally isolated from other sealable compartments, and thus particular drug delivery devices may be selectively heated, cooled, and/or made available to a user. The container may utilize thermoelectric heating and cooling control, and may further contain additional thermal mass to aid in energy efficiencies and reduce temperature fluctuations. Administration of the drug may be postponed to an appropriate time should the user be unable to take the drug at the prescribed time. The packaging may automatically reorder refills or remind the user to do so.

These approaches may allow for a user to interact with the container via any number of computing devices, for example, by computers, laptops, tablets, cellular telephones, and the like. A designated application on any of these devices may allow for the warming and/or cooling processes to be quickly initiated at any remote location due to the networking and communications capabilities of the storage compartment. Accordingly, the drug delivery device may be ready for usage immediately upon removing it from the storage container.

The storage container may be powered using any number of power sources which may provide charging and/or backup power thereto should a primary power source fail. As such, the risk of product degradation due to insufficient or temporarily nonexistent temperature control is minimized. The storage container may also be adapted to operate in a low-power mode in which a monitoring circuit is provided and activated upon opening the container. This may in turn cause at least one of the container sensor and the device sensor to be activated.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

It is understood that any of the features described herein with regards to a particular figure and/or embodiment may be incorporated into any or all of the remaining figures and/or embodiments. For example, one or two of the two networks 118, 122 of FIG. 1, may be utilized with the embodiments described in FIG. 6 to communicate with the computing device 640. Other examples are possible.

Figure 11:
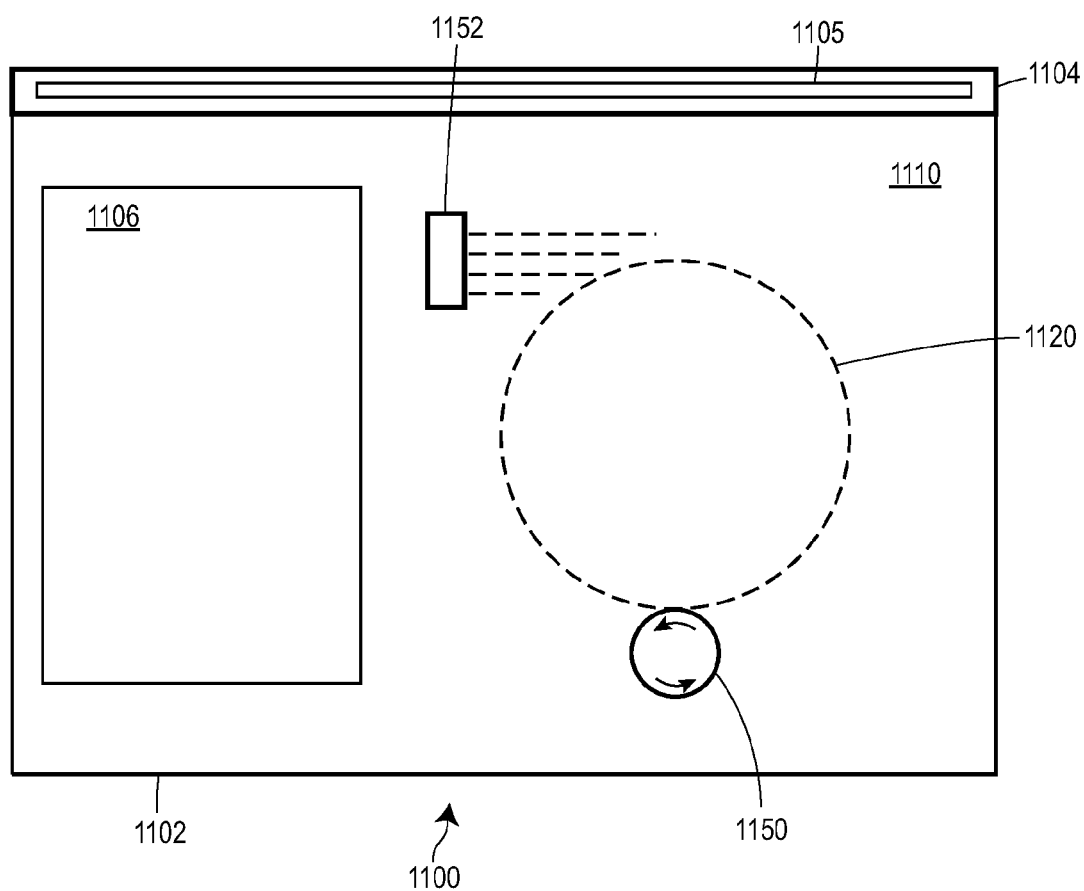
FIG. 11 comprises a cross-sectional view of an exemplary drug delivery system including a mixing device in accordance with various embodiments of the invention.

Referring now to FIG. 11, an alternate drug delivery system 1100 is provided. It will be understood that reference characters having the same two-digit suffixes (e.g., storage container 1102) represent previously described elements (e.g., storage container 302) and will not be discussed in substantial detail. It is further understood that any additional features described with regards to system 1100 may be used in combination with any of the systems and embodiments described in this disclosure. Specifically, the system 1100 may be viewed as at least a portion of the system illustrated in FIG. 1 or any other figures. In the alternate drug delivery system 1100, a storage container 1102 includes at least one storage container compartment 1110, a storage container lid 1104 having a slot 1105 for accommodating instructions for use or operation, a number of electronic components 1106, a drug delivery device 1120 adapted to deliver a drug to a user and to be at least partially disposed within one or more of the storage compartments 1110, a mechanical mixing apparatus 1150, and a fan 1152. It is understood that the system 1100 may include any number of additional components such as, for example any number of computing modules, processors, memories, and communication devices. Other examples are possible.

The electronic components 1106 may include any number of batteries, controllers, heating units, communications modules, sensors, displays, and the like. Other examples of electronic components discussed herein may be incorporated into the system 1100 as desired.

In this embodiment, the mechanical mixing apparatus 1150 may be a belt drive or roller apparatus coupled to suitable driving devices such as, for example, a motor (not shown). The drug delivery device 1120 may be positioned to rest on top of the mechanical mixing apparatus 1150 which may then rotate to mix the liquid medicament contained within the drug delivery device 1120. By mixing the medicament during heating process, localized overheating may be reduced. In this embodiment, the fan 1152 may generate airflow within the storage compartment 1110 to provide a uniform heating process.

In operation, a user may receive the medication and/or the drug delivery device 1120 and place it in the fully charged storage container compartment 1110. The user may then create a schedule which indicates when they would like the drug to be ready, and place the system 1100 into a refrigerator. It is understood that in some examples, the system 1100 may include cooling apparatuses, and thus may not need to be stored in a separate cooling device. When the schedule indicates a medication should be administered, a notification may be sent to the user who then confirms they wish to receive the medication.

Upon receiving the conformation, the system 1100 thermally isolates the drug delivery device 1120 from the refrigerator and begins warming the air in the storage compartment 1110 via convection as well as mixing the drug via the mechanical mixing apparatus 1150. The system 1100 may then switch to a temperature maintenance mode in which the desired temperature is maintained and alert the user of readiness for administration.

The temperature control may be set to maintain a temperature between approximately 20° C.-45° C. depending on the medicament and injection device. Generally speaking, a two to three degree range will be selected, and in particular, a range close to approximately 37° C. may be used to provide a comfortable administration experience.

Figure 12:
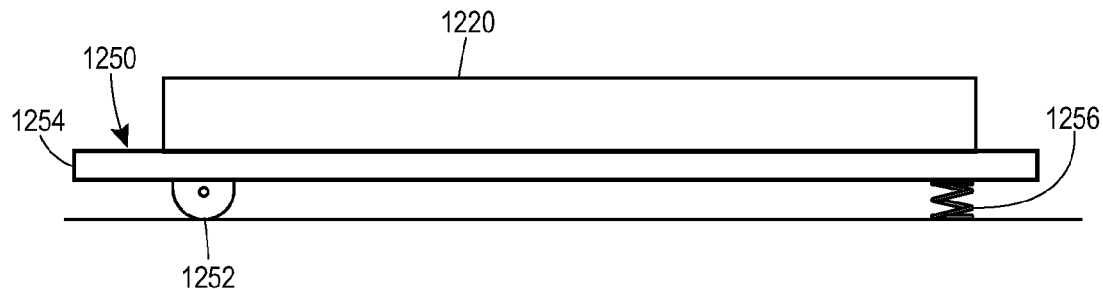
FIG. 12 comprises a cross-sectional view of an exemplary drug delivery system including an alternate mixing device in accordance with various embodiments of the invention.

In some examples, and as illustrated in FIG. 12, the mechanical mixing apparatus 1250 may mix the medicament stored in the drug delivery device 1220 via a rocking motion. The mechanical mixing apparatus 1250 may include a motor 1252 and a linear actuator 1254. The drug delivery device 1220 may rest on a portion of the linear actuator 1254. The motor 1252 may generate a torque which causes the drug delivery device 1220 to partially rotate in opposite directions, thus causing the fluid contained therein to slowly shift from side to side and be mixed.

In some examples, a spring 1256 or other similar device may act to cause the linear actuator 1254 to return to an original position. In these examples, the motor may periodically temporarily deactivate, thus causing the spring 1256 to urge the linear actuator 1254 to a tilted position where one end of the linear actuator 1254 moves towards a lower surface of the storage compartment. The motor may then activate and cause another end of the linear actuator 1254 to move towards the lower surface of the storage compartment. As a result, the movement of the linear actuator may resemble a rocking or see-saw motion.

In some examples, in lieu of using the spring 1256, the motor 1252 may be disposed at a location that is offset from the center of the mass of the drug delivery device 1220 so that the linear actuator 1254 naturally rests in a first angled position. The motor 1252 may then actuate in a manner that causes the linear actuator 1254 to move towards the second angled position, causing the medicament to be mixed. The motor 1252 may then deactivate, thus causing the linear actuator 1254 to move back to the first position. Other examples of mechanical mixing apparatuses 1250 are possible.

Figure 13A:
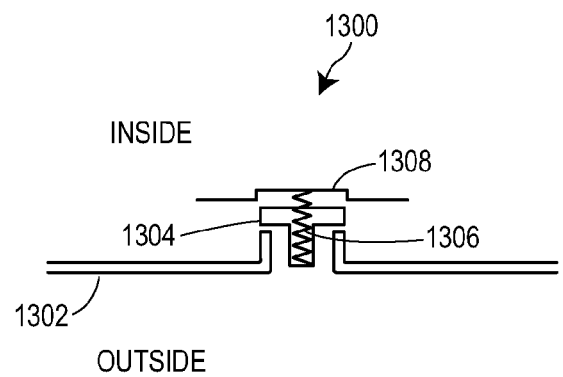
FIGS. 13A and 13B comprise cross-sectional views of, a thermal insulation system 1300 for a drug delivery system in accordance with various embodiments of the invention.
Figure 13B:
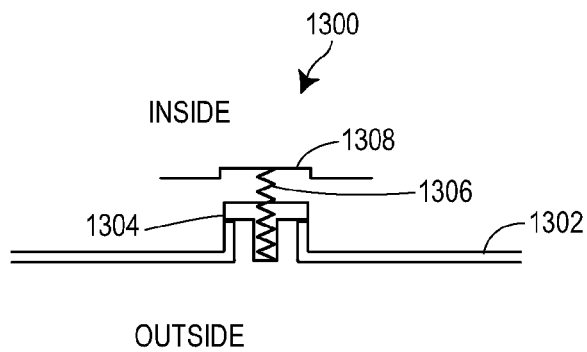

Referring to FIGS. 13A & 13B, a thermal insulation system 1300 for a drug delivery system is provided. It will be understood that the system 1300 may be used in combination with any of the previously-described systems, approaches, and/or embodiments described in this disclosure as desired. The system 1300 may include a thermally conductive case 1302 or surface, any number of sealing extensions 1304, a spring 1306, and an inner surface 1308.

The extension 1304 may be coated with a thermal insulator and may have a generally T-shaped cross-section. The extension 1304 may include an opening and comprise an outer shell defining a cavity. The spring 1306 may be constructed of a shape-memory alloy which is adapted to "remember" an original shape and/or configuration and return to this configuration upon being heated. In some examples, the shape-memory alloy may be a nitinol wire. Other examples are possible. The spring 1306 may be partially disposed within the cavity of the extension 1304 such that the spring 1306 rests on a lower surface and extends through the opening. In some examples, the inner surface 1308 is a surface of the storage compartment. For example, this surface may be the lower surface upon which the drug delivery device rests.

In operation, when the spring 1306 has a temperature below its transition temperature (e.g., when the system is in a refrigerated or cooled state), conduction between the case 1302 as well as convection between the interior and exterior of the system 1300 occurs. In this configuration, and as illustrated in FIG. 13A, the spring 1306 remains compressed, thus causing a gap between the ledges of the extension 1304 to allow for convection. When the user desires to administer the drug, the storage compartment is heated to a suitable temperature. When a threshold temperature is reached, as illustrated in FIG. 13B, the spring 1306 returns to a relaxed state where it exerts a force against the inner surface 1308. This force causes the extension 1304 to move towards the case 1302 and act as a seal to isolate the inner surface and the corresponding drug delivery device or devices from convection between the interior and exterior of the system 1300. Additionally, because the case 1302 is displaced from the inner surface 1308, conduction between the case 1302 and the inner surface 1308 is reduced and/or eliminated, thus further providing thermal isolation of the storage compartment.

The above description describes various systems and methods for use with a drug delivery device and its corresponding packaging. It should be clear that the system, drug delivery device and/or approaches may further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab);

M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-W10 Ulcerative Colitis mAb (MDX-1100); anti-LLY antibody; BMS-66513; anti-Mannose Receptor/hCG3 mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

What is claimed is:
1. A drug delivery system comprising:
a storage container defining one or more storage compartments;
at least one container sensor coupled to the storage container for sensing a condition of the at least one storage compartment;
a container condition change mechanism coupled to the storage container for imparting a change on one or more conditions of the one or more storage compartments;
at least one drug delivery device adapted to deliver a drug to a user and adapted to be at least partially disposed within one or more of the one or more storage compartments of the storage container;
at least one delivery device sensor coupled to the at least one drug delivery device for sensing a condition of the at least one drug delivery device;
a delivery device condition change mechanism coupled to the at least one drug delivery device for imparting a change on one or more conditions of the at least one drug delivery device; and
a controller coupled to the storage container and in communication with the at least one container sensor, and in communication with the at least one delivery device sensor when the at least one drug delivery device is disposed in one or more of the one or more storage compartments of the storage container,
wherein the controller includes a memory, a processor, and computer-executable instructions stored on the memory and executable by the processor to instruct at least one of (a) or (b):
(a) the container condition change mechanism to impart a change on the one or more conditions of the one or more storage compartments of the storage container,

(b) the delivery device condition change mechanism to impart a change on the one or more conditions of the at least one drug delivery device.

2. The drug delivery system of claim 1, wherein the at least one container sensor comprises at least one of:
   (a) a proximity sensor coupled to the storage container for sensing at least one of (i) a presence of the at least one drug delivery device and (ii) whether the storage container is in an open configuration,
   (b) a pressure sensor conductive switch disposed within the storage container for sensing whether the drug delivery device is disposed within the storage container,
   (c) a temperature sensor coupled to the storage container for sensing at least one of an external temperature and an internal temperature of the storage container,
   (d) a superelastic material adapted to engage a circuit when the storage container is within a temperature threshold, and
   (e) a humidity sensor for sensing a humidity within the one or more compartments of the storage container.

3. The drug delivery system of claim 1, wherein the at least one delivery device sensor comprises at least one of:
   (a) a temperature sensor for sensing a temperature of a drug stored in a reservoir of the drug delivery device,
   (b) a switch for detecting the position of a locking mechanism associated with an actuator of the drug delivery device,
   (c) a switch for detecting the position of a plunger mechanism associated with an actuator of the drug delivery device,
   (d) a switch for detecting the position of a needle cap on the drug delivery device,
   (e) a photo sensor for detecting at least one of an opacity and a color of a drug stored in a reservoir of the drug delivery device.

4. The drug delivery system of claim 1, wherein the container condition change mechanism comprises at least one of:
   (a) a heating mechanism adapted to raise the temperature of the one or more storage compartments,
   (b) a cooling mechanism adapted to lower the temperature of the one or more storage compartments,
   (c) a locking mechanism adapted to selectively restrict and permit access to the one or more storage compartments,
   (d) a vacuum pump mechanism adapted to draw a vacuum on one or more of the one or more storage compartments of the storage container,
   (e) a lock mechanism associated with selectively enabling access to one or more of the one or more storage compartments of the storage container,
   (f) a communication device adapted to communicate information relating to the drug delivery system.

5. The drug delivery system of claim 1, wherein the delivery device condition change mechanism comprises at least one of:
   (a) a locking mechanism adapted to selectively enable use of the drug delivery device,
   (b) a heating mechanism adapted to raise the temperature of at least a portion of the drug delivery device,
   (c) a cooling mechanism adapted to lower the temperature of at least a portion of the drug delivery device,
   (d) a communication device adapted to communicate information relating to the drug delivery system.

6. The drug delivery system of claim 1, wherein each of the one or more storage compartments of the storage container includes a sealing mechanism to selectively seal the storage compartment.

7. The drug delivery system of claim 1, wherein the storage container comprises a plurality of sealable storage compartments and a plurality of container sensors, each container sensor associated with one of the plurality of sealable storage compartments.

8. The drug delivery system of claim 1, wherein the plurality of sealable storage compartments are thermally isolated from each other.

9. The drug delivery system of claim 1, further comprising:
   a first communication module coupled to the storage container; and
   a computing device located separate from the storage container and the at one least drug delivery device, the computing device having a memory, a processor, computer-executable instructions stored on the memory, and a second communication module adapted to communicate with the first communication module;
   wherein the controller instructs the first communication module to transmit a signal to the second communication module of the computing device and wherein the computing device is adapted to determine and transmit a corresponding signal via the second communication module to the first communication module to instruct the at least one of (a) or (b), as recited in claim 1:
      (a) the container condition change mechanism to impart a change on the one or more conditions of the one or more storage compartments of the storage container,
      (b) the delivery device condition change mechanism to impart a change on the one or more conditions of the at least one drug delivery device.

10. The drug delivery system of claim 9, wherein the storage container is adapted to restrict the first communication module from transmitting the signal to the computing device when the storage container is in a closed configuration.

11. The drug delivery system of claim 9, wherein the first communication module transmits the signal via a wireless communication protocol.

12. The drug delivery system of claim 9, wherein the signal transmitted to the computing device includes information relating to at least one of:
   (a) a temperature excursion experienced within the storage container,
   (b) a frequency of use of the delivery device, and
   (c) a quantity of unused delivery devices.

13. A method for managing a plurality of drug delivery devices stored in a plurality of compartments in a storage container, the method comprising:
   obtaining a sensing condition data of at least one storage compartment;
   obtaining a container condition change data for imparting a change of one or more conditions data for each of the plurality of compartments of said storage container;
   obtaining a drug delivery device condition data of each drug delivery device;
   obtaining a delivery device condition change data for imparting a change of one or more conditions data for each of the plurality of drug delivery devices, wherein each delivery device is configured to deliver a drug to a user and is configured to be at least partially disposed within a compartment of the storage container;

obtaining data from each of the plurality of drug delivery devices stored in the storage container using a controller coupled to the storage container;

determining, based on the obtained data, which of the plurality of drug delivery devices to effect an action upon; and selectively instructing at least one of:

(a) a container condition change mechanism coupled to the container to impart a change on one or more conditions of the plurality of compartments, b) a drug delivery device condition change mechanism coupled to at least one delivery device to impart a change on one or more conditions of the drug delivery device.

14. The method of claim 13, wherein selectively instructing the container change mechanism to impart a change comprises at least one of:

(a) displaying, via a display, information relating to the sensed condition, (b) adjusting the temperature of at least one of the plurality of compartments in the storage container, (c) restricting access to the storage container by locking a lid, (d) granting access to the storage container by unlocking a lid, (e) providing, via an alert device, a user with information relating to at least one drug delivery device, (f) selectively granting access to a particular drug delivery device stored in a particular compartment, (g) logging the sensed condition;

(h) transmitting the sensed condition to a remote computing device;

(i) determining an appropriate time to use the drug delivery device.

15. The method of claim 14, wherein displaying information relating to the sensed condition comprises displaying at least one of:

(a) an indication that the at least one drug delivery device is ready for use;

(b) an indication of when the at least one drug delivery device will be ready for use;

(c) an indication of a quantity of drug delivery devices remaining for use.

16. The method of claim 13, wherein selectively instructing the delivery device change mechanism to impart a change comprises at least one of:

(a) selectively adjusting a temperature of at least one drug delivery device, (b) selectively enabling at least one of the drug delivery devices, (c) selectively enabling at least one of the drug delivery devices in response to user identity information input received from a user;

(d) selectively disabling at least one of the drug delivery devices, (e) selectively disabling at least one of the drug delivery devices, at least until verifying identity information received via user input;

(f) communicating an enabled/disabled status of at least one of the drug delivery devices to the alert device.

17. The method of claim 13, wherein at least one container sensor is adapted to detect at least one of:

(a) a presence of the drug delivery device in the compartment, (b) whether the storage container is in an open or closed configuration, (c) whether the storage container is in a sealed or unsealed configuration, (d) a temperature of at least one drug delivery device, (e) an ambient temperature surrounding the storage container, (f) an internal temperature within the storage container, (g) a temperature differential between the ambient temperature and the internal temperature.

18. The method of claim 13, wherein at least one delivery device sensor obtains data from each of the plurality of drug delivery devices, wherein the obtained data comprises at least one of:

(a) a quantity of drug contained within the at least one drug delivery device, and (b) a temperature of the at least one drug delivery device.

19. The method of claim 13, wherein the data obtained and selective instructions are communicated via a wired and/or a wireless communication protocol.

20. The method of claim 13, wherein a controller is adapted to:

read identification information for each of the plurality of drug delivery devices;

compare the identification information of each of the plurality of drug delivery devices; and identify a drug delivery device amongst the plurality of drug delivery devices as having an earliest expiration date.

* * * * *

UNITED STATES PATENT AND TRADEMARK OFFICE
CERTIFICATE OF CORRECTION

PATENT NO. : 11,207,460 B2
APPLICATION NO. : 15/775650
DATED : December 28, 2021
INVENTOR(S) : Ferry Tamtoro et al.

It is certified that error appears in the above-identified patent and that said Letters Patent is hereby corrected as shown below:

In the Claims

At Column 47, Line 11, "b)" should be -- (b) --.

At Column 47, Line 30, "condition;" should be -- condition, --.

At Column 47, Line 32, "device;" should be -- device, --.

At Column 48, Line 5, "user;" should be -- user, --.

At Column 48, Line 10, "input;" should be -- input, --.

Signed and Sealed this
Twenty-second Day of November, 2022

Katherine Kelly Vidal
*Director of the United States Patent and Trademark Office*